(12) United States Patent
Staniforth et al.

(10) Patent No.: US 7,089,934 B2
(45) Date of Patent: Aug. 15, 2006

(54) DELIVERY OF ORAL DRUGS

(75) Inventors: John Staniforth, Bath (GB); Michael Tobyn, Wiltshire (GB)

(73) Assignee: Vectura Limited, Wiltshire (GB)

( * ) Notice: Subject to any disclaimer, the term of this patent is extended or adjusted under 35 U.S.C. 154(b) by 682 days.

(21) Appl. No.: 09/793,304

(22) Filed: Feb. 26, 2001

(65) Prior Publication Data

US 2001/0020147 A1 Sep. 6, 2001

(30) Foreign Application Priority Data

Feb. 28, 2000 (GB) .................................. 0004701.9
Apr. 12, 2000 (GB) .................................. 0009023.3

(51) Int. Cl.
*A61M 15/00* (2006.01)
*A61M 16/00* (2006.01)
*B65D 83/06* (2006.01)
*A61M 13/00* (2006.01)
*A61M 16/10* (2006.01)

(52) U.S. Cl. ........................... 128/203.15; 128/203.12; 128/203.21; 128/204.18; 604/58

(58) Field of Classification Search ........... 128/203.12, 128/203.15, 204.18, 203.21, 203.18; 604/58
See application file for complete search history.

(56) References Cited

U.S. PATENT DOCUMENTS

| | | | |
|---|---|---|---|
| 4,805,811 A | 2/1989 | Wetterlin | 222/337 |
| 4,981,468 A | 1/1991 | Benefiel et al. | 604/83 |
| 5,002,048 A * | 3/1991 | Makiej, Jr. | 128/200.23 |
| 5,080,649 A * | 1/1992 | Vetter | 604/91 |
| 5,169,029 A * | 12/1992 | Behar et al. | 222/1 |
| 5,207,217 A | 5/1993 | Cocozza et al. | 128/203.21 |
| 5,263,475 A | 11/1993 | Altermatt et al. | 128/203.15 |
| 5,505,196 A | 4/1996 | Herold et al. | 128/203.15 |
| 5,533,505 A * | 7/1996 | Kallstrand et al. | 128/203.15 |
| 5,568,884 A | 10/1996 | Bruna | 222/189.09 |
| 5,665,068 A * | 9/1997 | Takamura | 604/90 |
| 5,692,644 A * | 12/1997 | Gueret | 222/80 |
| 5,702,362 A | 12/1997 | Herold et al. | 604/58 |
| 5,715,810 A * | 2/1998 | Armstrong et al. | 128/203.15 |
| 5,881,720 A * | 3/1999 | Vinogradov et al. | 128/203.15 |
| 5,906,202 A * | 5/1999 | Schuster et al. | 128/203.23 |
| 6,432,381 B1 * | 8/2002 | Liversidge et al. | 424/1.29 |
| 6,484,718 B1 * | 11/2002 | Schaeffer et al. | 128/203.15 |
| 6,531,152 B1 * | 3/2003 | Lerner et al. | 424/464 |

FOREIGN PATENT DOCUMENTS

| | | |
|---|---|---|
| EP | 0518087 A1 | 12/1992 |
| EP | 0518087 B1 | 7/1995 |
| GB | 2165159 | 4/1986 |
| WO | WO 92 09322 | 6/1992 |
| WO | WO 93 03785 | 3/1993 |
| WO | WO 95 34337 | 12/1995 |

(Continued)

*Primary Examiner*—Henry Bennett
*Assistant Examiner*—Andrea M. Ragonese
(74) *Attorney, Agent, or Firm*—Davidson, Davidson & Kappel, LLC

(57) ABSTRACT

Disclosed is a system for delivery of a drug comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 µm to about 1 mm such that an effective dose of said drug cannot be delivered into the lower lung of a human patient. Also disclosed are novel methods, devices and dosage forms for delivering a drug.

27 Claims, 18 Drawing Sheets

FOREIGN PATENT DOCUMENTS

| | | |
|---|---|---|
| WO | WO 96 23485 | 8/1996 |
| WO | WO 98 48875 | 11/1998 |
| WO | WO 00 64520 | 11/2000 |

* cited by examiner

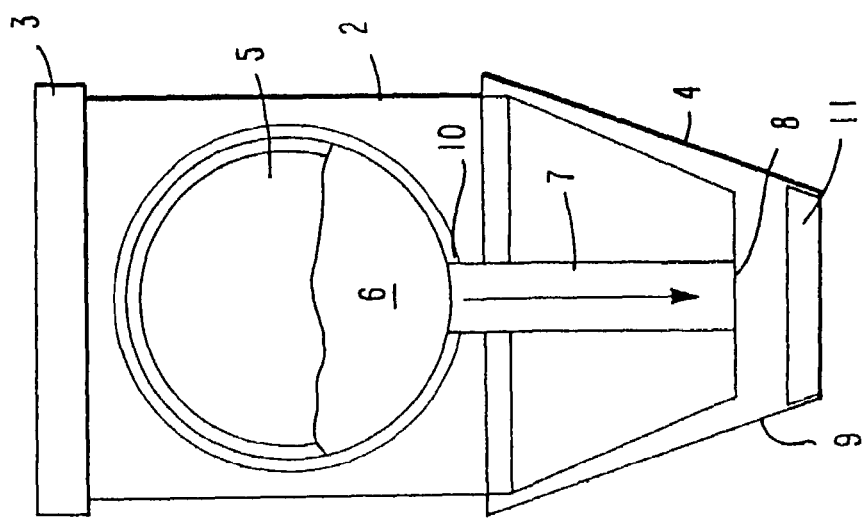
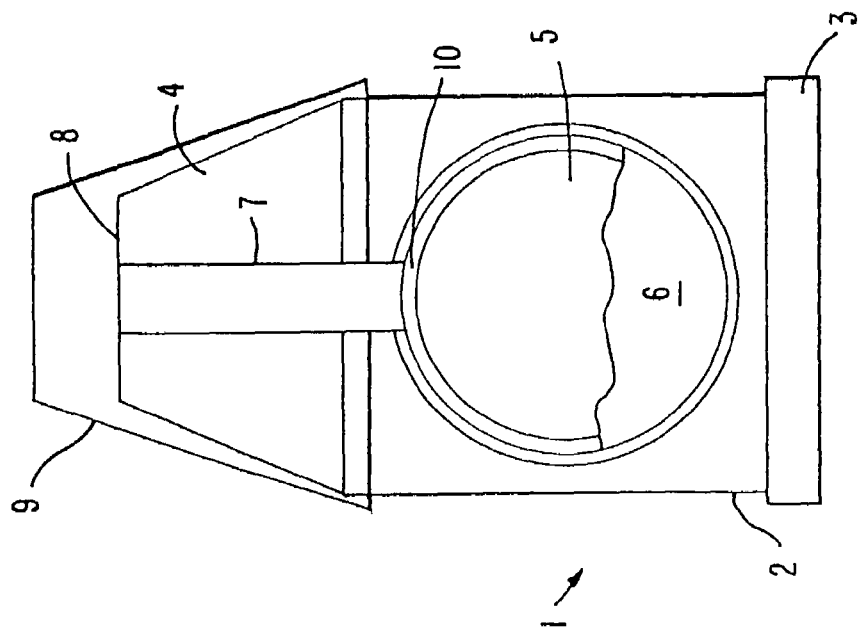

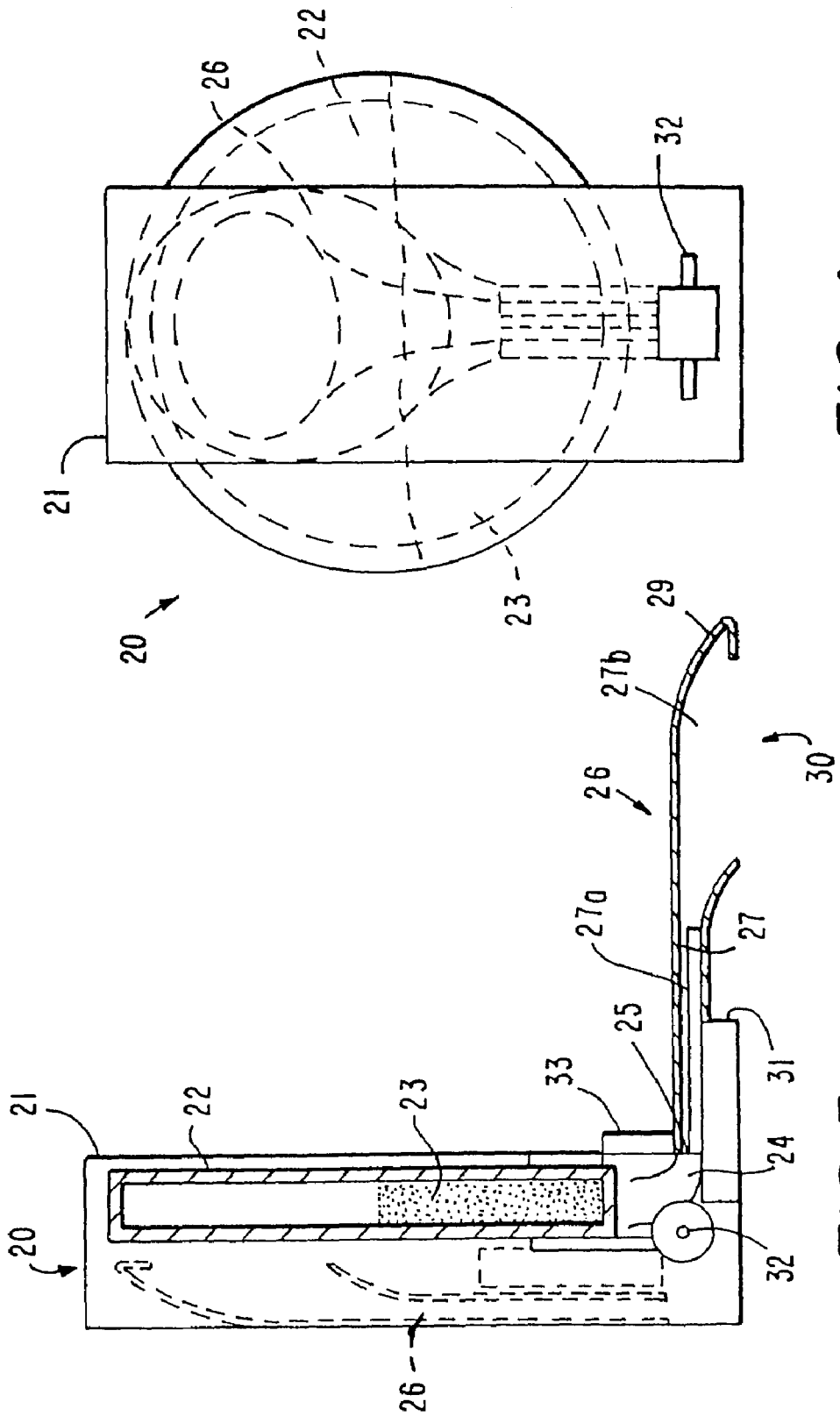

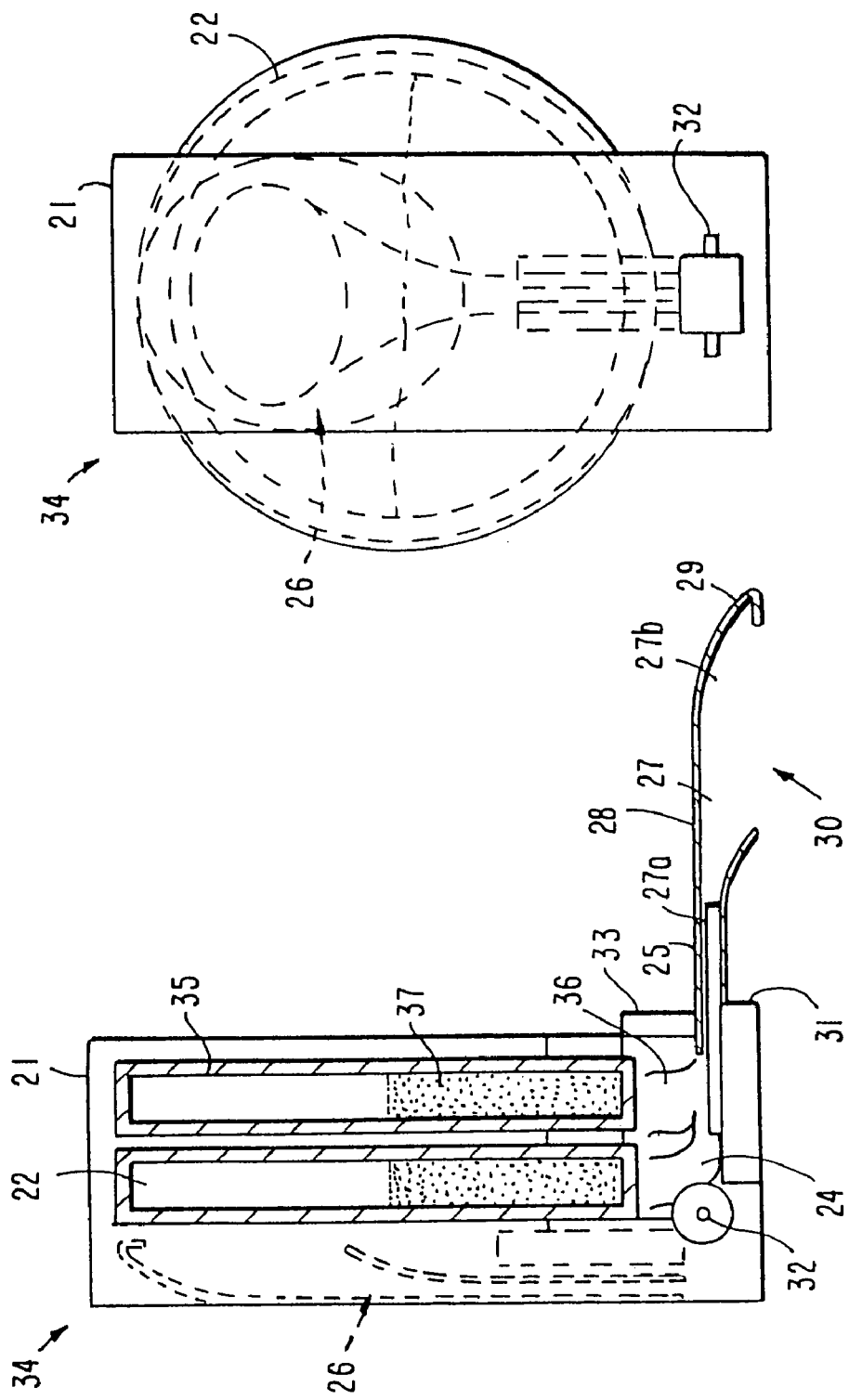

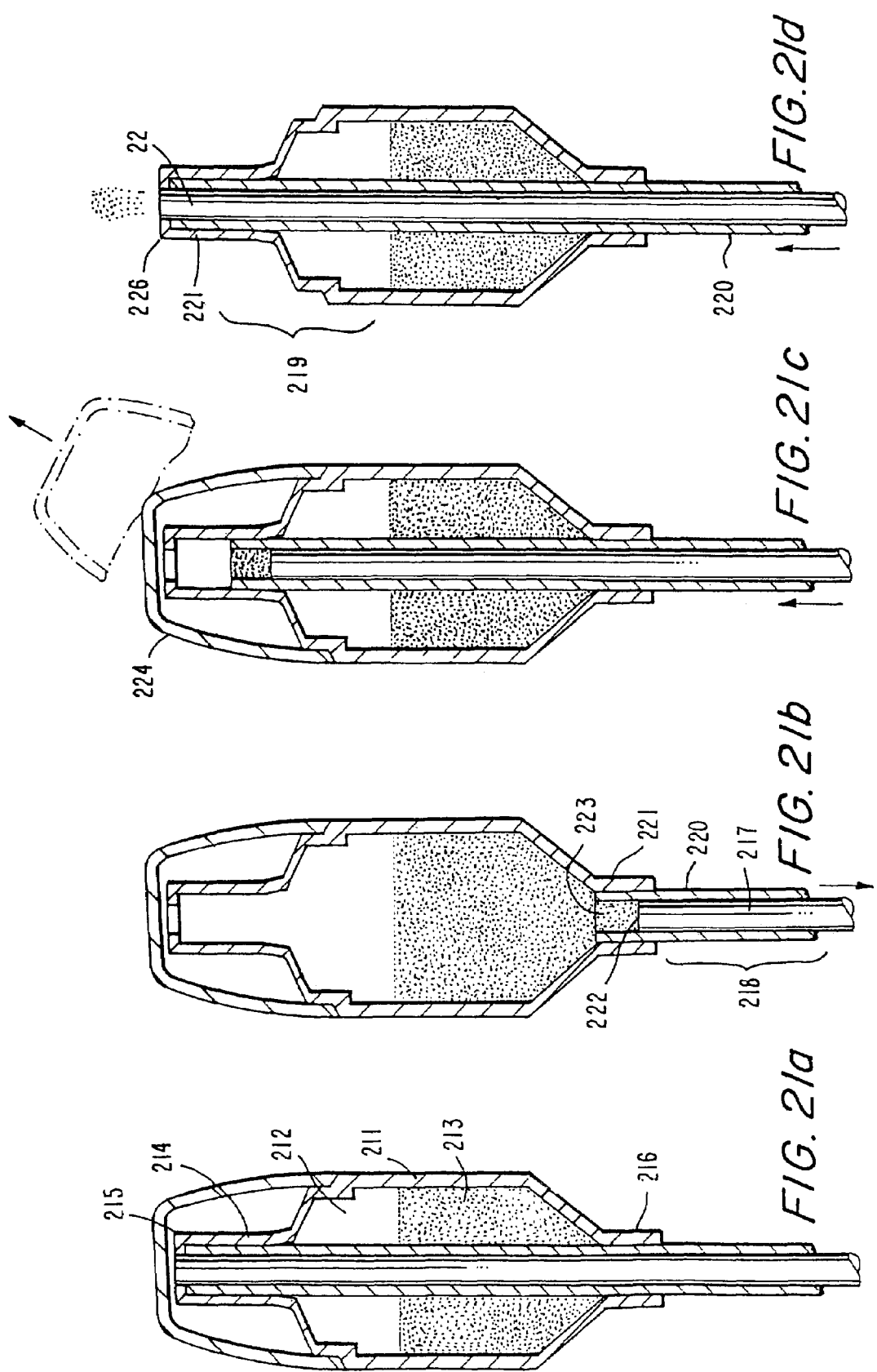

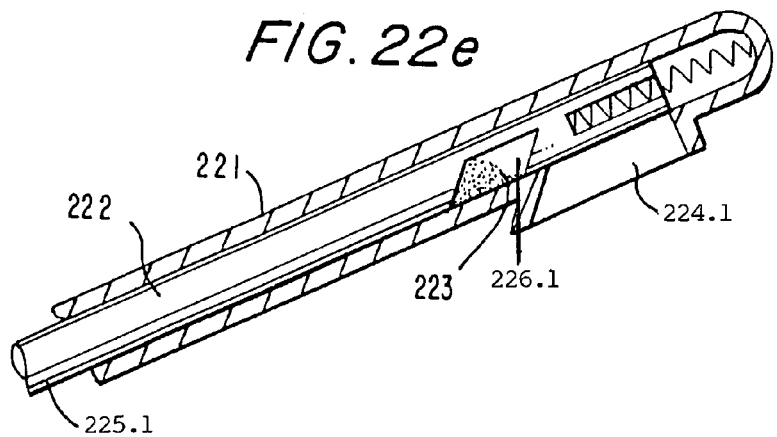
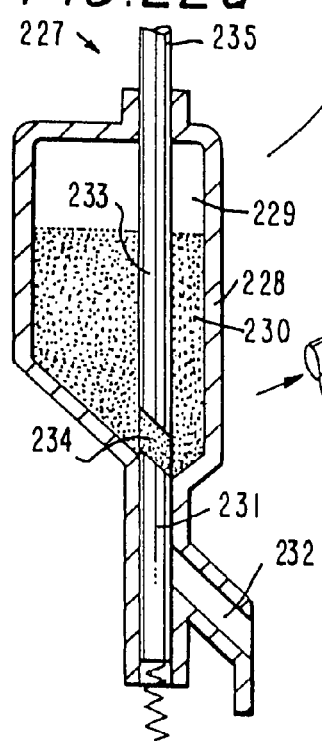
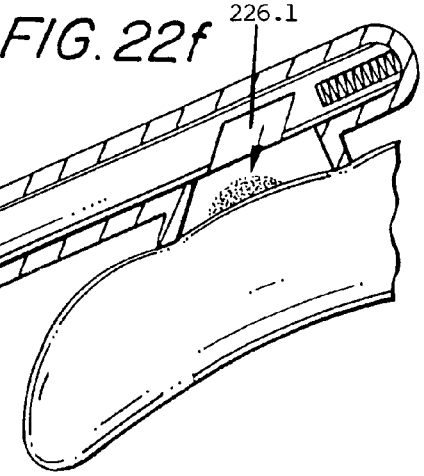
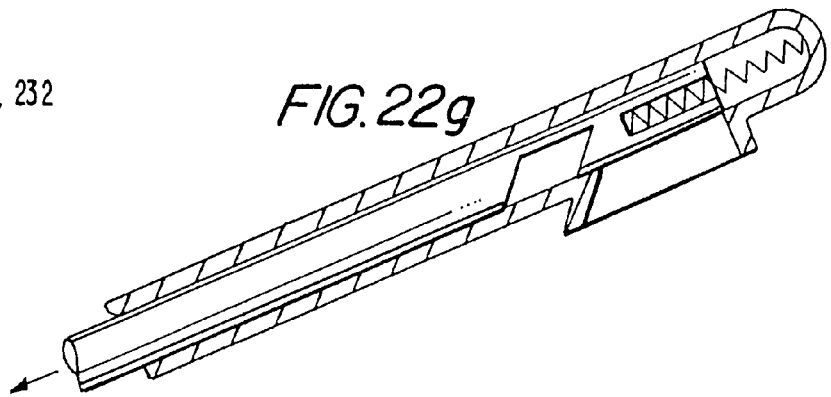

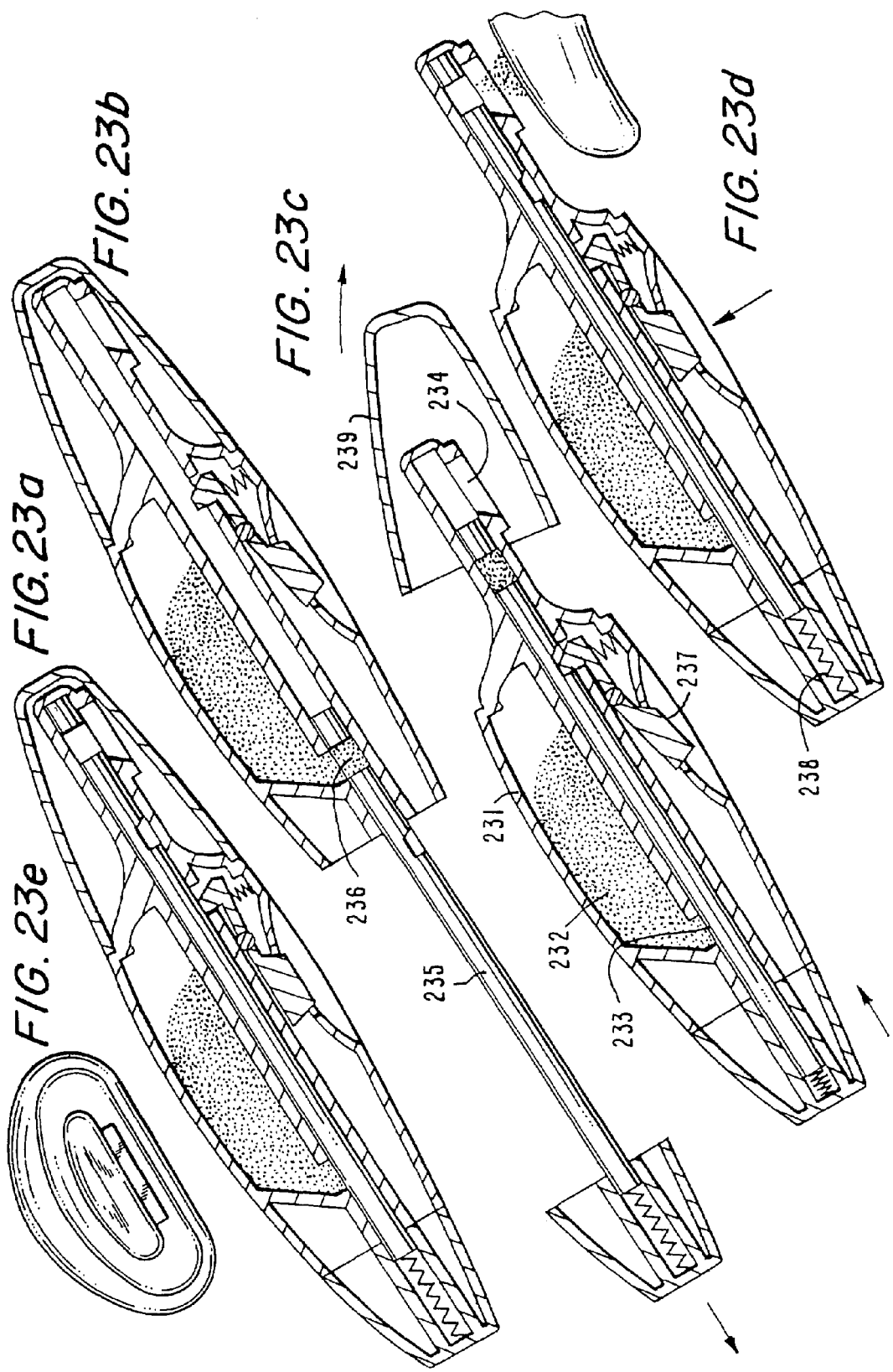

DELIVERY OF ORAL DRUGS

FIELD OF THE INVENTION

The present is directed to a delivery device and method for the oral administration of therapeutic agents in powder form for gastrointestinal deposition.

BACKGROUND OF THE INVENTION

The most prominent mode of delivery of therapeutic agents is by the oral route by means of solid dosage forms such as tablets and capsules. Oral administration of solid dosage forms is more convenient and accepted than other modes of administration, e.g. parenteral administration. However, the manufacture, dispensing and administration of solid dosage forms are not without associated problems and drawbacks.

With the manufacture of solid dosage forms, in addition to the active agent, it is necessary to combine other ingredients in the formulations for various reasons, such as to enhance physical appearance, to provide necessary bulk for tableting or capsuling, to improve stability, to improve compressibility or to aid in disintegration after administration. However, these added excipients have been shown to adversely influence the release, stability and bioavailability of the active ingredient. The added excipients are a particular problem with drugs which require a high dose in order to provide a therapeutic effect, e.g., biphosphonate drugs. The inclusion of the additional excipient can make the final tablet extremely large which could result in esophogeal damage due to the physical characteristics of the dosage form if it is not swallowed properly. Esophogeal damage can also be caused by toxicity caused by the drug itself, if the tablet becomes lodged in the throat or has an increased transit time through the esophagus, due to its increased size.

Further, the tableting of certain drugs has many associated production problems. In particular, many drugs, e.g., acetaminophen, have poor compressibility and cannot be directly compressed into solid dosage forms. Consequently, such drugs must either be wet granulated or manufactured in a special grade in order to be tableted which increases manufacturing steps and production costs.

The adherence to good manufacturing practices and process controls is essential in order to minimize dosage form to dosage form and batch to batch variations of the final product. Even strict adherence to these practices still is not a guarantee that acceptable variation will occur.

With the high cost of industrial scale production and governmental approval of solid dosage forms, such formulations are often available in a limited number of strengths, which only meet the needs of the largest sectors of the population. Unfortunately, this practice leaves many patients without acceptable means of treatment and physicians in a quandary with respect to individualizing dosages to meet the clinical needs of their patients.

The dispensing of oral solid dosage forms also makes the formulations susceptible to degradation and contamination due to repackaging, improper storage and manual handling.

There are also many patients who are unable or unwilling to take conventional orally administered dosage forms. For some patients, the perception of unacceptable taste or mouth feel of a dose of medicine leads to a gag reflex action that makes swallowing difficult or impossible. Other patients, e.g., pediatric and geriatric patients, find it difficult to ingest typical solid oral dosage forms, e.g., due to tablet size.

Other patients, particularly elderly patients, have conditions such as achlorhydria which hinders the successful use of oral solid dosage forms. Achlorhydria is a condition wherein there is an abnormal deficiency or absence of free hydrochloric acid in the gastric secretions of the stomach. This condition hinders the disintegration and/or dissolution of oral solid dosage forms, particularly dosage forms with high or insoluble excipient payloads Flavored solutions/suspensions of some therapeutic agents have been developed to facilitate the oral administration of oral agents to patients normally having difficulty ingesting conventional solid oral dosage forms. While liquid formulations are more easily administered to the problem patient, liquid/suspension formulations are not without their own significant problems and restrictions. The liquid dose amount is not as easily controlled compared with tablet and capsule forms and many therapeutic agents are not sufficiently stable in solution/suspension form. Indeed, most suspension type formulations are typically reconstituted by the pharmacist and then have a limited shelf life even under refrigerated conditions. Another problem with liquid formulations which is not as much a factor with tablets and capsules is the taste of the active agent. The taste of some therapeutic agents is so unacceptable that liquid formulations are not a viable option. Further, solution/suspension type formulations are typically not acceptable where the active agent must be provided with a protective coating, e.g. a taste masking coating or an enteric coating to protect the active agent from the strongly acidic conditions of the stomach.

Another alternative to oral dosage forms for certain medications is aerosol dosage forms which administer therapeutic agents for deposition to the pulmonary system. The use of aerosol dosage forms has many advantages for the patient. The packaging of the active agent is convenient and easy to use, generally with limited manual manipulation. As the medicine is sealed within the device, direct handling of the medication is eliminated and the contamination of the contents from air and moisture can be kept to a minimum. Further, a metering valve can be included in the device in order to individualize the dose for particular patients. However, such formulations also have drawbacks such as decreased bioavailability of the drug due to improper administration by the patient. For example, if a patient's breathing is not coordinated with the activation of the device, the active agent will not reach its intended site of action which will lead to a decrease in therapeutic benefit.

Another alternative is dry powder dosage forms. For example, International Patent Application WO 94/04133, hereby incorporated by reference, describes a powder composition for inhalation which contains a microfine drug such as salbutamol sulfate and a carrier containing an anti-static agent. The carrier is calcium carbonate or a sugar, especially lactose. The amount of carrier is 95–99.99 weight percent. The compositions are said to be useful for delivery of the active agent to the lungs while providing reduced side effects such as nausea by maximizing its proportion of drug reaching the lungs.

U.S. Pat. No. 4,590,206, hereby incorporated by reference, describes capsules, cartridges or aerosol containers containing spray-dried sodium cromoglycate in finely divided and un-agglomerated form. A substantial proportion of the individual drug particles have sizes and shapes which allow deep penetration into the lung and yet are free-flowing so as to allow capsule filling.

International Patent Application WO 93/25198, hereby incorporated by reference, is directed to an ultrafine powder for inhalation. The powder comprises a drug and hydroxypropyl cellulose and/or hydroxypropylmethylcellulose. More than 80 weight percent of the particles in the powder are said to have a particle diameter of 0.5–10 microns. The powder is said to be able to reach the lower windpipe and bronchi.

Due to the disadvantages of known drug delivery discussed above (as well as other disadvantages) there exists a need in the art for the development of a device and method for facilitating delivery of a wide range of therapeutic agents for gastrointestinal deposition and which minimize pulmonary deposition of materials having undesirable or unknown pulmonary toxicology but which are approved for oral delivery.

OBJECTS OF THE INVENTION

It is an object of the invention to provide a method and system for the delivery of a dose of a therapeutic agent in multiparticulate form for gastrointestinal deposition.

It is an object of the invention to provide a method and system for the oral administration of a dose of a therapeutic agent in multiparticulate form into the oral cavity of a patient for gastrointestinal deposition.

It is an object of the invention to provide a method and system for the dispensing of a dose of a therapeutic agent in multiparticulate form, for subsequent administration into the oral cavity for gastrointestinal deposition.

It is a further object of the invention to provide a method and system for delivery of multiple doses of a therapeutic agent in multiparticulate form which minimizes the need for inert pharmaceutical excipients.

It is a further object of the invention to provide a method and system for delivery of multiple doses of a therapeutic agent in multiparticulate form for fast, standard, sustained, controlled, or targeted release.

It is a further object of the invention to provide a method and system for the delivery of a dose of a therapeutic agent for gastrointestinal deposition which protects the active ingredient from contamination and moisture.

It is a further object of the invention to provide a method and system for the delivery of a dose of a therapeutic agent for gastrointestinal deposition which allows for the dosing to be adjustable based on the needs of an individual patient or patient population.

It is a further object of the invention to provide a method and system for the delivery of a dose of a therapeutic agent for gastrointestinal deposition which can be used for a wide variety of agents for a wide variety of therapies, e.g. to treat systemic and/or local conditions.

It is a further object of the invention to provide a method and system for the delivery of two or more different drugs in multiparticulate form simultaneously or at different times. The device of the system can hold the 2 or more drugs in separate compartments or together in the same compartment.

It is a further object of the invention to provide a method and system for the delivery of a dose of a therapeutic agent for gastrointestinal deposition which provides an acceptable variability from dose to dose and batch to batch.

It is a further object of the invention to provide a method of producing a unit dose of a drug without limitation to the compressibility or dose amount of the drug.

It is a further object of the invention to provide a method and system for the delivery of a dose of a therapeutic agent for gastrointestinal absorption which can be administered and swallowed without the aid of a fluid.

It is a further object of the invention to provide novel oral dosage forms in multiparticulate form.

The above objects of the invention and others are achieved by virtue of the present invention, which in certain embodiments provides a drug delivery system for delivery of a drug for gastrointestinal deposition. The system comprises a multiple unit dosing device comprising a housing and an actuator, the device containing multiple doses of multiparticulates comprising drug particles, the device upon actuation delivering a unit dose of the multiparticulates for gastrointestinal deposition, the multiparticulates having a mean particle size of greater than 10 μm and preferably less than about 1 mm in order to minimize pulmonary deposition of the multiparticulates and such that an effective dose of the drug cannot be delivered into the lower lung of a human patient. The drug delivery system can be used to administer the unit dose of multiparticulates into the oral cavity of the patient (in-vivo) or to dispense the unit dose into an intermediate receptacle (ex-vivo) for subsequent gastrointestinal deposition.

In certain embodiments, the invention provides a device for delivery of a drug comprising a housing and an actuator, the device capable of containing multiple doses of multiparticulates comprising drug particles, the device upon actuation capable of delivering a unit dose of the multiparticulates wherein the multiparticulates have a mean diameter of greater than 10 μm, and preferably less than about 1 mm in order to minimize pulmonary deposition of the multiparticulates and such that an effective dose of the drug cannot be delivered into the lower lung of a human patient. The device can be used to administer the unit dose of multiparticulates into the oral cavity of the patient (in-vivo) or to dispense the unit (lose into an intermediate receptacle (ex-vivo) for subsequent gastrointestinal deposition.

In certain embodiments, the invention provides a device for delivering multiple unit doses of a drug in multiparticulate form comprising a housing for containing multiple unit doses of a multiparticulates comprising drug particles, the housing having an opening for delivering a unit dose of the multiparticulates; a metering component operable between a first position in which it receives a unit dose from said housing and a second position in which it delivers the unit dose of drug to the opening in the housing; the unit dose being delivered from the device to the exterior of the device through the opening of the housing with an air flow of less than about 20 liters/min. In preferred embodiments the device does not include a propellant to facilitate the delivery of the unit dose and preferably the unit dose is delivered through the opening substantially by gravitational force.

In certain embodiments, the invention provides a device for delivering multiple unit doses of a drug in multiparticulate form comprising a housing to contain multiple unit doses of multiparticulates comprising drug particles, the housing having a mouthpiece for delivering a unit dose of the multiparticulates into the oral cavity of a patient; means for removing a unit dose of the multiparticulates from the housing and delivering the unit dose to the mouthpiece, the mouthpiece having a drug receiving end connected to the removing means and a drug delivery end through which the unit dose is delivered outside the device, the mouthpiece being positioned on the device such that drug particles expelled through the mouthpiece can be deposited in the oral cavity of a patient substantially without deposition of drug particles into the lungs of the patient.

In certain embodiments, the invention provides a device for delivering multiple unit doses of a drug in multiparticulate form comprising a housing to contain multiple unit doses of multiparticulates comprising drug particles; the housing having a mouthpiece for delivering a unit dose of the multiparticulates into the oral cavity of a patient; a metering component for removing a unit dose of the multiparticulates from the housing and delivering the unit dose to the mouthpiece, the mouthpiece having a drug receiving end connected to the metering component and a drug delivery end through which the unit dose is delivered outside the device, the mouthpiece being positioned on the device such that drug particles expelled through the mouthpiece can be deposited in the oral cavity of a patient substantially without deposition of the drug particles the lungs of the patient.

In certain embodiments, the invention provides a method of preparing a drug delivery system for delivering multiple doses of a drug for gastrointestinal deposition comprising preparing a multiparticulate drug formulation in a manner to provide particles which when placed in the oral cavity and swallowed are deposited to the gastrointestinal tract and not deposited in any substantial amount to the lungs; and placing multiple unit doses of said drug formulation in a device which meters a single unit dose for delivery.

In certain embodiments, the invention provides a method of treating a patient in need of multiple doses of a drug for gastrointestinal deposition comprising preparing multiparticulates comprising drug particles in a manner wherein the drug particles when placed in the oral cavity and swallowed are deposited to the gastrointestinal tract and not deposited in any substantial amount to the lungs; placing multiple unit doses of the multiparticulates in a device which meters a single unit dose for delivery; and either (a) administering the unit dose into the oral cavity of a patient or (b) dispensing the unit dose into an intermediate receptacle and thereafter administering the unit dose into the oral cavity of the patient.

In certain embodiments, the invention provides a drug formulation for gastrointestinal deposition comprising a non-compressed free flowing plurality of particles comprising a drug and a pharmaceutically acceptable excipient, the particles having a mean diameter of greater than 10 µm to about 1 mm, the particles comprising at least about 80% drug, preferably at least about 90% drug.

In certain embodiments, the drug formulation can further comprise a facilitating agent (e.g., an absorbability enhancer, a texture modifier, a taste masking agent, a sweetener, a flavorant, a salivary stimulant, an effervescent compound or combinations thereof) which enhances the oral administrability of the unit dose.

In certain embodiments, the drug formulation can further comprise a material to provide fast, standard, sustained, controlled, or targeted release.

In certain embodiments, the invention provides a method for delivery of a drug comprising delivering multiparticulates comprising drug particles via the use of a multiple unit dosing device comprising a housing and an actuator, the device upon actuation delivering a unit dose of the multiparticulates, and thereafter re-using said device to deliver additional unit doses of multiparticulates at appropriate dosing intervals, the drug particles having a mean diameter of greater than 10 µm, and preferably less than about 1 mm to minimize pulmonary deposition and such that an effective dose of the drug cannot be delivered into the lower lung of a human patient. In certain embodiments of the method, upon actuation, the delivery is by administering the unit dose into the oral cavity of the patient (in vivo). Alternatively upon actuation, the delivery is the dispensing of the unit dose into an intermediate receptacle (ex vivo) for subsequent gastro-intestinal deposition.

In certain embodiments of the invention, greater than about 80% of the unit dose is deposited in the gastrointestinal tract, preferably greater than about 90% or greater than about 95%, and most preferably, about 100% of the unit dose is deposited in the gastrointestinal tract.

In preferred embodiments of the invention, the unit dose comprises a discreet collection of multiparticulates. For purposes of the invention, a “discreet collection” means that the multiparticulates are in the form of a non-compressed free flowing unit and not dispersed in a cloud or mist, which effectively minimizes inhalation of the active agent into the lungs of the patient. The unit dose can be, e.g., from about 0.01 mg to about 1.5 g, depending on the dose of the active agent being delivered. For example, the unit dose can be from about 1 mg to about 100 mg or from about 10 mg to about 50 mg. Preferably, the unit dose is administered to the tongue, most preferably towards the front of the tongue behind the teeth, where it can be easily swallowed with or without the need for an additional fluid. However the invention does contemplate delivery to any portion of the tongue, taking into account, e.g., the taste sensations of different sections of the tongue and/or individual patient preference associated with comfort, e.g. mouth position.

In certain embodiments of the invention, the mean diameter of the drug particles is of a size which minimizes their capacity to be inhaled into the lower lung. Typically, the agglomerate mean particle size of the drug particles is greater than 10 μm, preferably greater than about 50 μm or greater than about 75 μm. In certain embodiments of the invention, the mean particle size range of the drug particles is from about 100 μm to about 1 mm. In preferred embodiments, greater than 80% of the drug particles have the above disclosed diameter (not mean diameter), e.g. 80% of the drug particles have a diameter of greater than 10 μm, or a diameter of from about 100 μm to about 1 mm. In other embodiments, greater than about 90% of the drug particles have the above disclosed diameter.

In certain embodiments of the invention, the mean diameter of the drug particles does not vary by greater than about 20%, preferably not greater than about 15% and most preferably not greater than about 10%.

In certain embodiments of the invention, the multiparticulates comprise a pharmaceutically acceptable excipient. The excipient preferably does not comprise more than about 20% of the multiparticulates by weight, preferably not more than about 10% by weight.

In certain embodiments of the invention, the excipient is coated with the drug, or the drug is coated with the excipient. Alternatively, the drug and the excipient can be a mixture of powders, each preferably being greater than 10 μm, preferably greater than about 50 μm or greater than about 75 μm.

In certain embodiments of the invention, the excipient can provide taste masking of the drug. In taste masking embodiments and other embodiments, the excipient can include flavors and/or sweeteners. In other embodiments, the excipient can provide a sustained or delayed release of the drug.

In certain embodiments of the invention, the multiple doses of the drug are contained in a reservoir. The reservoir can contain an amount of multiparticulates to provide any number of unit doses, e.g. from about 2 doses to about 400 doses. For ease in patient compliance, the reservoir has a sufficient quantity of to provide e.g. a days supply, a months supply or a years supply of doses, e.g. 30 or 365 for once daily dosing for a month or year, respectively.

In certain embodiments, the system can contain multiple dosing mechanisms in order to provide different dosage amounts for different times. For example, the system can comprise two dosing mechanisms which can provide a different dosage amount in the morning and the evening. In other embodiments, the dosing mechanism can be adjusted in order to increase or decrease the size of the dose.

In certain embodiments, the system can contain more than one reservoir, each containing a different drug or enantiomeric form of drug. Upon actuation, the desired amount of each drug is metered out for delivery, such metering being present in the factory or other place, e.g., a pharmacy. Such a system would be beneficial for combination therapy and would eliminate the need for multiple systems and would allow a much wider range of possible doses and dose combinations than hereto possible.

In certain embodiments of the invention, the system delivers up to about 80%, preferably up to about 90% of the doses supplied in the system, thus eliminating waste by providing an efficient system.

In certain embodiments of the invention, the variability between dose to dose is not greater than 5%. In certain embodiments of the invention, the delivery of the unit dose is facilitated by a gas, which may be provided by the patients own breath maneuvers or which can be contained in the system in the form of pressurized gas or liquid gas. Alternatively, the delivery of the unit dose can be facilitated by a liquid carrier. In such an embodiment, the liquid and the unit dose are mixed during or after the unit dose is discharged from the reservoir.

In certain embodiments of the invention, the device comprises a mouthpiece. Preferably, the mouthpiece is of sufficient length to minimize moisture exposure of the reservoir from outside the device. Preferably, the mouthpiece comprises a mouthpiece cap or closure to minimize the ingress of moisture (e.g., from saliva or humidity) into the device. In order to minimize moisture exposure of the reservoir, the invention can also include a desiccant. Further measures can be taken by making the device from a material which has water repellant properties to inhibit the accumulation of moisture. For example, the device can consist of a non-wetting material such as silicone, which if contaminated with moisture, would promote the formation of droplets which would run off and not adhere to the surface of the device and would not result in the accumulation of water. In certain embodiments, the device (especially the mouthpiece) can comprise a silver containing plastic or other material resistant to microbial growth.

In order to aid in patient compliance, certain embodiments of the invention include a counter or indicator to display the number of doses remaining in the system or the number of doses actuated.

In certain embodiments of the invention, the unit doses are individually metered prior to actuation, e.g., in the form of capsules or blisters, wherein each blister contains one individual unit dose. The system can be capable of containing any multiple of pre-metered unit doses, e.g. from about 2 to about 400 blisters.

In certain embodiments of the invention, the system is capable of being reloaded with additional doses (in reservoir or pre-metered form) upon full or partial depletion. Alternatively, the system can be manufactured wherein the device is disposable and is not capable of being reloaded with additional unit doses.

The present invention is also directed to a method of administering a drug to a patient for gastrointestinal deposition comprising formulating the drug in multiparticulate form; containing the multiparticulates in a drug delivery device capable of delivering multiple unit doses of the multiparticulates into the oral cavity; administering a unit dose of the multiparticulates to the oral cavity of the patient wherein greater than about 80% of the drug is deposited in the gastrointestinal tract. This method can be achieved, e.g., by controlling at least one at least one of the following factors: a) formulating the multiparticulates to have a mean diameter of greater than 10 µm; b) administering the multiparticulates with a device having a mouthpiece which directs the multiparticulates onto the tongue of the patient; c) administering the multiparticulates with a device which delivers the unit dose as a discreet collection; and d) administering the multiparticulates with a device having a flared mouthpiece.

The invention is also directed to methods of delivery (e.g., in vivo administration and ex vivo dispensing) and methods of treatment utilizing any of the disclosed embodiments directed to compositions of matter. The invention is also directed to methods of preparation of all of the disclosed embodiments.

The present invention is also directed to systems which contain particles greater than 10 µm of a particulate drug and particles of 10 µm or less of the same or a different drug which upon actuation, deliver a unit dose for oral and pulmonary administration.

The present invention is also directed to mouthpieces adapted to fit onto a drug delivery device for administering a drug in multiparticulate form into the oral cavity of a patient, the improvement being that the mouthpiece protrudes from the drug delivery device at an angle in order to direct the multiparticulates onto the tongue of the patient.

The present invention is also directed to mouthpieces which are conical or rectangular in shape and which provide a flared opening, wherein the area of the outlet of the mouthpiece is larger than the area of the inlet of the mouthpiece. This reduces the velocity of the delivered multiparticulates in order to minimize pulmonary deposition.

The present invention is also directed to mouthpieces and devices which drop the unit dose vertically onto the tongue with minimal or no horizontal velocity. This action directs the unit dose down to the tongue and minimizes movement of particles toward the back of the throat in order to minimize or avoid pulmonary deposition. In preferred embodiments, when the device is utilized as intended, greater than 80% of the unit dose is administered from the device in a downward direction from about 45 degrees to about 135 degrees based on a vertical baseline independent of the device. Preferably greater than 90% of the drug follows this direction.

The invention is also directed to methods of providing a therapeutic effect to a patient comprising administering to the patient a unit dose of a drug utilizing the systems, devices and formulations disclosed herein. The invention is also directed to methods of preparing the systems, devices and formulations disclosed herein.

The invention is also directed to novel powders for oral administration which are disclosed herein.

For purposes of the present invention, the term "device" refers to an apparatus capable of delivering a unit dose of drug.

The term "system" refers to a drug delivery device in combination with the disclosed multiparticulate drug having the specifications disclosed herein, e.g. drug particle size, excipient type, etc.

The term "discreet collection" refers to a non-compressed free flowing unit of multiparticulates with minimal particulate matter being dispersed in the surrounding environment (e.g., as a cloud or mist).

The term "drug" refers to any agent which is capable of providing a therapeutic effect to a patient upon gastrointestinal deposition. This encompasses all drugs which are intended for absorption for a systemic effect (regardless of their actual bioavailability) as well as drugs intended for a local effect in the gut and/or oral cavity, e.g. nystatin, antibiotics or local anesthetics.

The term "particle size" refers to the diameter of the particle.

The term "deposition" means the deposit of the unit dose at the intended point of absorption and/or action. For example, gastrointestinal deposition means the intended deposit of the unit dose in the gastrointestinal system for e.g., absorption for a systemic effect or to exert a local effect. Pulmonary deposition means the intended deposit of drug into the lungs in order to provide a pharmaceutical effect, regardless that the unit dose may enter the oral cavity prior to pulmonary deposition.

The term "dispense", when used in connection with the devices and systems of the present invention, means that the device or system delivers the unit dose ex vivo with the intent of subsequent administration to a mammal. For example, the device or system can dispense the unit dose into a food, a liquid, a spoon, or another intermediate receptacle.

The term "administer", when used in connection with the devices and systems of the present invention, means that the device or system delivers the unit dose in vivo, i.e., directly into the gastrointestinal tract of a mammal.

The term "deliver" is meant to cover all ex vivo and in vivo delivery, i.e., dispensing and administering, respectively.

The term "patient" refers to humans as well as other mammals in need of a therapeutic agent, e.g., household pets or livestock. This term also refers to humans or mammals in need of or receiving prophylactic treatment.

In certain embodiments, the particulates are defined functionally with respect to the fact that they are of a size such that an effective dose cannot be delivered into the lower lung of a human patient. However, this definition should be understood to mean that a small percentage of drug (but not an amount effective to render a therapeutic effect) may in fact be inadvertently delivered to the lungs of the patient. Also, this definition is meant to define the particles, but not to limit the use of the invention to the treatments of humans only. The invention may be used for delivering doses of drugs to other mammals as well.

BRIEF DESCRIPTION OF THE DRAWINGS

FIG. 1 is a schematic side view of a delivery device according to the invention in an upright position; and FIG. 2 is a schematic side view of the device of FIG. 1 in the inverted (delivery) position.

FIG. 3 is a vertical section through another form of delivery device according to the invention having a mouthpiece;

FIG. 4 is a front view of the device of FIG. 3, with the mouthpiece folded into a storage position;

FIG. 5 is a vertical section through a third form of delivery device according to the invention, having a mouthpiece;

FIG. 6 is a front view of the device of FIG. 5 with the mouthpiece folded into a storage position.

FIG. 23 is an illustration of a powder delivery device with an internal reservoir.

DETAILED DESCRIPTION

Figure 7:
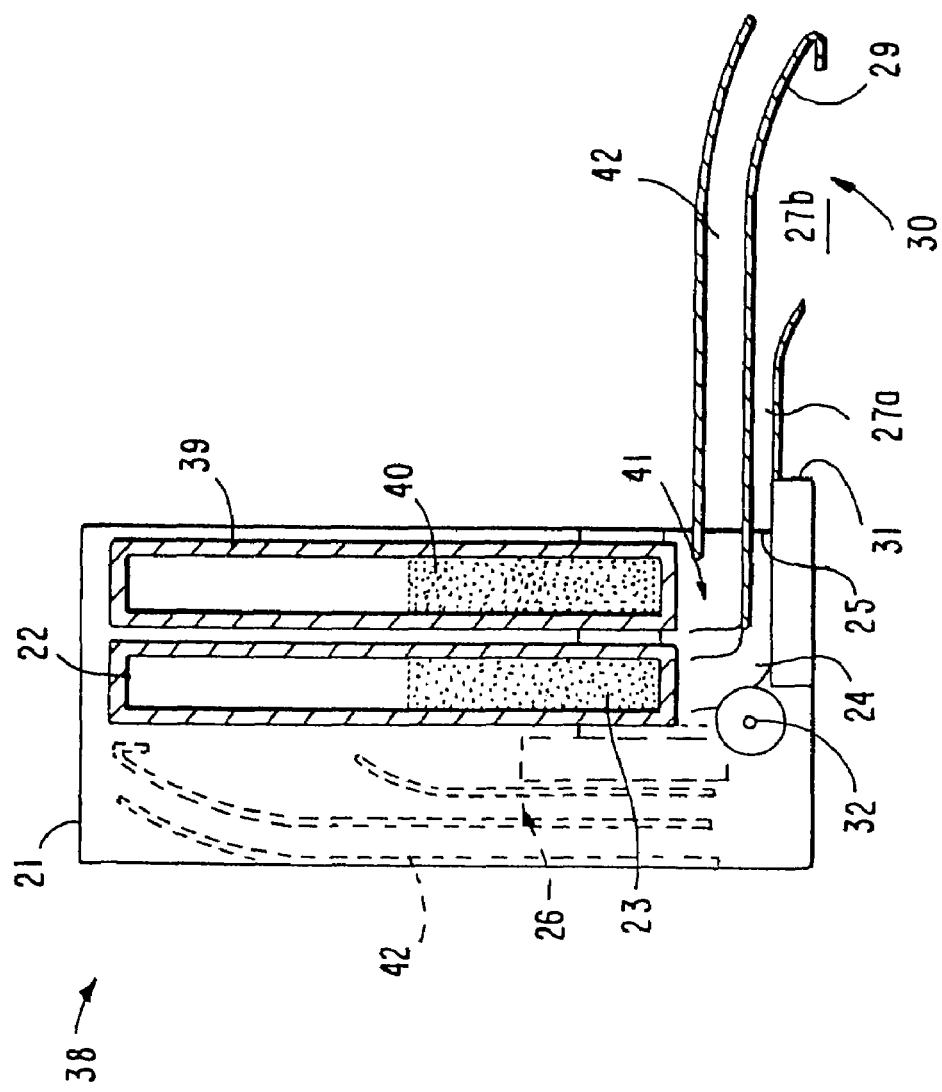
FIG. 7 is a vertical section through a fourth form of delivery device according to the invention.

In general, it has been recognized in the art that dry powder inhalation or insufflation formulations must consist of particles of a size of about 2 microns in diameter in order for the particles, when inhaled, to reach the peripheral or "deep" lung, including alveoli. Particles larger than 10 microns in diameter are not able to reach the deep lung when inhaled because they are collected on the back of the throat and upper airways in humans. Therefore, known powder delivery systems have been formulated with particle sizes of less than 10 microns in order for the particles to reach the intended site of action, the pulmonary system. Known powder delivery devices have not contemplated delivery of particles from a multi-dose delivery device to achieve gastrointestinal deposition, and therefore have avoided the use of drag particles having a large size, e.g. greater than 10 microns. By virtue of the present invention, it has been a surprising discovery that drug particles greater than 10 microns can be delivered from a multi-use drug delivery device for gastrointestinal deposition in a patient in order to minimize the inhalation of the drug particles into the lungs, in order to have substantially all of the dose deposited in the gastrointestinal system.

The present invention is directed to a system comprising a device containing multiple doses of a drug which is in multiparticulate form. When the system is actuated, the device delivers a unit dose, preferably by administration into the oral cavity of a patient, for the unit dose to be deposited in the gastrointestinal system of the patient for subsequent absorption and/or action. Preferably, the unit dose is subsequently swallowed by the patient for absorption and/or action in the stomach and/or intestines. However, the system can be used to deliver a unit dose of drug intended for sublingual or buccal absorption and/or action.

In order to increase gastro-intestinal deposition and reduce pulmonary deposition, the unit dose is preferably administered as a discreet collection. Administration of the unit dose as a discreet collection ensures that the multiparticulates are aggregated together and there is no dispersion or "mist" which forms in the oral cavity which would tend to be aspirated into the lungs.

The mean drug particle size of the unit dose is greater than 10 µm and preferably greater than about 50 µm in order to minimize pulmonary aspiration of the drug such that an effective dose of said drug cannot be delivered into the lower lung of a human patient. For example, the drug particles can be greater than about 75 µm, or greater than about 100 µm. A preferred range of the mean drug particle size is about 100 µm to about 500 µm, although drug particles of 1 mm and above would still be functional in the present invention. Preferably, any inactive particle in the unit dose is also greater than 10 µm in order to minimize pulmonary aspiration of such particles.

In order to achieve the desired mean particle size, the active material can be incorporated into larger particles if the active agent itself is less than 10 µm. This can be performed by known procedures in the art, e.g., by granulation, coating, agglomeration or spray coating. The larger particles may include excipients suitable for use in pharmaceutical formulations.

The present invention is also directed to systems which contain drug particles greater than 10 µm and drug particles of less than 10 µm of the same or a different drug which upon actuation, administer a unit dose for oral and pulmonary administration. For example, when gastrointestinal deposition is desired the drug will formulated, e.g., to have at least 95% by weight of the gastrointestinal dose being of aerodynamic diameter of at least 50 µm. For the inlialable dose, the drug will be in the form of multiparticulates of which at least 90% by weight of the inhalable dose has an aerodynamic diameter of not more than 10 µm. These particles can be arranged as to be releasable from larger carrier particles.

The gastric dose and the inhalable dose can be incorporated into a single formulation comprising carrier particles; the inhalable drug being on the surface of the carrier particles and releasable therefrom on inhalation from the device; and the larger particles being for gastrointestinal deposition. The two doses can be contained in the same reservoir or can be contained separately and co-administered upon actuation.

In preferred embodiments of the invention, the mean drug particle size of the multiparticulates does not vary by more than about 20%, more preferably no more than about 15% and most preferably by no more than about 10%. Preferably, any inactive particles will also be within this range.

In preferred embodiments, greater than about 80% of the drug particles fall within the above disclosed variance, more preferably greater than 90% and most preferably about 100% of the drug particles fall within the above disclosed ranges. For example, in a preferred embodiment, about 90% of the drug particles of the unit dose would have a mean particle size of about 450 to about 550 µm, although this example is not meant to be limiting. Preferably, any inactive particles also fall within this range.

The size of the unit dose is dependent on the amount of drug needed to provide the intended therapeutic effect and the amount of any pharmaceutically acceptable excipient which may be necessary. Typically, a unit dose of from about 0.01 mg to about 1.5 g would be sufficient to contain a therapeutically effective amount of the drug to be delivered, however, this range is not limiting and can be smaller or higher, depending on the amount of drug and excipient that is necessary. Generally, the unit dose should not be so large that it is not capable of being swallowed by the patient without much difficulty. It is preferred that the unit dose is of a small enough quantity that it can be swallowed without the necessity of an additional liquid, however, the invention is not limited to such quantity and doses which may require a liquid are contemplated by the invention. Preferably the unit dose is from about 1 mg to about 100 mg, or from about 10 mg to about 50 mg, depending on the potency of the active agent. In situations where the unit dose is too large to be easily swallowed, it is contemplated that the system can be actuated multiple times for subsequent delivery in order to administer divided doses of the intended dose, which are more easily swallowed by the patient.

When it is contemplated for the unit dose to be swallowed without the use of an additional liquid, certain embodiments of the invention provide that the multiparticulates comprise an effective amount of an agent which stimulates the production of saliva in order to facilitate the swallowing of the unit dose. Such agents include any acid which is safe for human consumption and includes food acids, acid anhydrides and acid salts. Food acids include tartaric acid, malic acid, fumaric acid, adipic acid, and succinic acids and fruit acids, e.g., citric acid. Acid anhydrides of the above described acids may also be used. Acid salts may include sodium, dihydrogen phosphate, disodium dihydrogen pyrophosphate, acid citrate salts and sodium acid sulfite.

In other embodiments of the invention, the multiparticulates can comprise an effervescent compound or composition which provides a pleasing organoleptic effect which can substantially mask the taste of unpalatable active ingredients in the powder. The effervescent action also acts as a stimulant to saliva production. Effervescent agents include compounds which evolve gas. The preferred effervescent agents evolve gas by means of chemical reactions which take place upon exposure to a liquid such as saliva in the mouth. This bubble or gas generating chemical reaction is most often the result of the reaction of an acid (e.g. the saliva stimulant acids listed above) and an alkali metal carbonate/dicarbonate or base. The reaction of these two general classes of compounds produces carbon dioxide gas upon contact with saliva.

The use of acids and/or effervescent ingredients is particularly useful in patients with achlorhydria or other patients with a problem swallowing the unit dose without the use of a liquid.

For ease of swallowing and in order to minimize pulmonary aspiration of multiparticulates, the system preferably is configured to dispense the unit dose onto the tongue of the patient. The tongue can be stuck out in order to facilitate the deposit of the unit dose thereon or preferably, the dispenser can be configured in order to deposit the unit dose on the tongue without the necessity of the patient sticking out the tongue. Preferably, the system is of such a configuration that the unit dose is deposited behind the teeth towards the front of the tongue. The front of the tongue is preferred in order to stimulate the natural swallowing of the unit dose into the esophagus. This reduces the possibility of any individual particles becoming airborne and inhaled into the pulmonary system and facilitates the swallowing of the unit dose by initiating a more natural swallowing reflex. However, the unit dose should be able to be placed anywhere on the tongue, including the deposit on the back of the tongue without stimulating the soft palate to cause a gag reflex.

As with most pharmaceutical formulations, it is often necessary to add a pharmaceutically acceptable excipient to the drug. For example, when formulating an agent into tablets or capsules, a bulking agent is used in order to provide enough mass to tablet or capsule the agent. This results in many of the drawbacks of solid dosage forms which were discussed above.

With the present invention, however, it is not necessary to have a large percent of the formulation consisting of excipient as it is preferable to have the unit dose which is deposited on the tongue of the patient as small as possible in order to facilitate swallowing. The use of excipient is used in the present invention, e.g., to improve flowability, to taste mask, to stimulate flow of saliva for swallowing or to provided a modified release of the drug. In preferred embodiments the excipient is less than about 20% by weight of the multiparticulates and more preferably less than about 10% by weight of the multiparticulates. These preferred percent weights of excipients are not meant to be limiting. For example, with a micro-dose drug such as digoxin or levothyroxine, the percent of excipient may need to be more than 20% in order to provide enough bulk for acceptable flow or dose metering characteristics.

The pharmaceutical acceptable excipient of the multiparticulates can coat the drug. In such an embodiment, the excipient can provide a modified release of the drug. For example, such a multiparticulate can be formulated to provide a delayed release wherein the drug is released in the intestine. Multiparticulate with an excipient coating can also be formulated in order to provide a sustained release of the drug over time in the gastrointestinal tract. Coating the drug with excipient can also be done in order to mask the bitter taste of certain drugs.

Alternatively, the excipient can be used as a substrate and the drug can be coated onto the excipient. This formulation option can be used in order to provide desired flow capabilities and to provide a critical mass of the drug particles in order to minimize lung aspiration.

The excipient can also be used in a mixture with the in order to provide the desired properties (e.g., flow properties) to allow the unit dose to be delivered as a discreet unit, with minimal multiparticulates suspended in the air.

When the multiparticulates are formulated as controlled release powders, the drug may be combined with a polymer which may be soluble, insoluble, permeable, impermeable or biodegradable. The polymers may be polymers or copolymers. The polymer may be a natural or synthetic polymer. Natural polymers include polypeptides, polysaccharides and alginic acid. A suitable polypeptide is zein and a suitable polysaccharide is cellulose. The drug/polymer combination can be formed by known methods such as granulating, spray coating or agglomerating.

Representative synthetic polymers include alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes and polyurethanes and co-polymers thereof. The polymer to be used is governed by its toxicity and its compatibility with the particular active ingredient being used and can be selected without difficulty by those skilled in the art.

Particularly suitable polymers include: methyl cellulose, ethyl cellulose, hydroxypropyl cellulose, hydroxypropyl methyl cellulose, hydroxybutyl methyl cellulose, cellulose acetate, cellulose propionate (lower, medium or higher molecular weight), cellulose acetate propionate, cellulose acetate butyrate, cellulose acetate phthalate, carboxymethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene glycol), poly(ethylene oxide), poly(ethylene terephthalate), poly(vinyl alcohol), poly(vinyl isobutyl ether), poly(vinyl acetate), poly(vinyl chloride) and polyvinylpyrrolidone. Especially suitable co-polymers include: butyl methacrylate/isobutyl methacrylate co-polymer, high molecular weight, methylvinyl ether/maleic acid co-polymer, methylvinyl ether/maleic acid, monoethyl ester co-polymer, methylvinyl ether/maleic anhydride co-polymer and vinyl alcohol/vinyl acetate co-polymer.

Representative biodegradable polymers include, polylactides, polyglycolides, poly(ethylene terephthalate), polyhydroxy-butyrate, polyhydroxy-valerate and polyurethane.

Representative acrylates and methacrylates are polyacrylic and methacrylic polymers such as those sold under the Trademarks Eudragit. Amberlite and Carbopol.

Classes of drugs which are suitable in the present invention include antacids, antiinflammatory substances, coronary dilators, cerebral dilators, peripheral vasodilators, antiinfectives, psychotropics, anti-manics, stimulants, anti-histamines, laxatives, decongestants, vitamins, gastro-intestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, drugs affecting calcification and bone turnover and anti-uricemic drugs.

Specific drugs include gastro-intestinal sedatives such as metoclopramide and propantheline bromide; antacids such as aluminum trisilicate, aluminum hydroxide, ranitidine and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland dysfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; and calcification affecting agents such as biphosphonates, e.g., etidronate, pamidronate, alendronate, residronate, teludronate, clodronate and alondronate.

Drugs which possess taste and/or odor characteristics which, when administered orally without any excipients, render the drug or therapeutic agent unpalatable to a subject and would be candidates for taste masking in the present invention include, but are not limited to, $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, prostaglandins, antidiuretic agents and the like. Typical drugs include but are not limited to nizatidine, cimetidine, ranitidine, famotidine, roxatidine, etinidine, lupitidine, nifentidine, niperitone, sulfotidine, tuvatidine, zaltidine, erythromycin, penicillin, ampicillin, roxithromycin, clarithromycin, psylium, ciprofloxacin, theophylline, nifedipine, prednisone, prednisolone, ketoprofen, acetaminophen, ibuprofen, dexibuprofen lysinate, flurbiprofen, naproxen, codeine, morphine, sodium diclofenac, acetylsalicylic acid, caffeine, pseudoephedrine, phenylpropanolamine, diphenhydramine, chlorpheniramine, dextromethorphan, berberine, loperamide, mefenamic acid, flufenamic acid, astemizole, terfenadine, certirizine, phenytoin, guafenesin, N-acetylprocainamide HCl, pharmaceutically acceptable salts thereof and derivatives thereof.

Dry powder inhalation devices require high air flow to create shear conditions sufficient to isolate discrete drug particles in the pulmonary system. The greater the air flow, the more the device disperses the powdered drug into smaller, more respirable particles. This air flow is in the range of about 20 liters/min. to about 150 liters/min. and results in high shear forces on agglomerates of drug and causes collisions between the agglomerates of powdered drug both of which tend to deagglomerate the large agglomerates into the desired primary particles for pulmonary deposition. In certain embodiments of the present invention, the air flow provided is enough to facilitate the unit dose of drug out of the device, but not enough in order to project the particles into a "mist" for inhalation into the pulmonary system. This air flow is less than 20 liters/min, preferably less than about 10 liters/min. In the present invention, devices from the prior art can be modified in order to provide the desired less than 20 liters/min. airflow. In alternate embodiments, there is minimal air flow and the powder dispenses from the device into the oral cavity through gravitational force or mechanical action. In certain embodiments, the unit dose is metered and mechanically moved to the dispensing hole of the device (against or in the direction of gravity) prior to dispensing.

In certain embodiments, the multiparticulates are contained in a reservoir. Preferably, the reservoir contains multiple doses of the multiparticulates in order to provide a multiplicity of unit doses. The number of unit doses contained in the reservoir and capable of being delivered by the system depends on, among other factors, the frequency of dosing and the duration of therapy of the drug being dispensed. For example, for acute therapy, the system can be configured to deliver 30 unit doses of an antibiotic being prescribed three times daily for 10 days. Alternatively for chronic therapy, the system can be configured to contain 30, 100 or even 365 doses of an antihypertensive drug administered once daily.

In certain embodiments, the system of the invention can be configured wherein the reservoir is replaceable, e.g., in the form of a replaceable cartridge, or wherein the reservoir is capable of being refilled, e.g., by including a removable plug wherein bulk powder can be introduced. However, in embodiments wherein the system is capable of being refilled, it is preferable that the system utilizes a replaceable system such as the previously disclosed cartridge device rather than refilling the system with bulk powder through an unplugged hole as the latter may be more prone to human error, e.g., loss of powder due to spilling or improper manipulation. Further, the handling of bulk powders may result in contamination of the reservoir, powder or both with moisture and/or contaminants.

In other embodiments the system can be disposable, wherein after administration of all of the unit doses, the system is not capable of being replaced with additional unit doses of the drug. This embodiment can be beneficial for many reasons. Most prominently, a disposable system will give the patient, the prescriber and the manufacturer, greater assurances that the patient is receiving a proper dosage from a functional system that has not been subjected to improper handling and/or internal friction for a long duration of time. Such a disposable device may also reduce the overall cost of manufacture, as the device would only have to be manufactured to provide an accurate dose for a finite period of time. With refillable systems, greater care would have to be taken in the manufacturing process and materials selected in order to assure that the device is capable of providing an accurate dose for a longer period of time, e.g. over a year. As a compromise between the disposable and refillable system, a refillable system can be manufactured wherein the patient is informed that after a certain amount of time and/or courses of therapy, the system should be replaced with a new device. Such a system would be beneficial to the patient, prescriber and manufacturer by reducing manufacturing cost, improving patient convenience by being able to refill the device and assuring to all parties that a patient will not be using a device which may be non-functional due to internal friction and/or improper handling.

In certain embodiments, a counter can be included in the system which can improve compliance of the patient. This is done by the count or indicator being utilized to know how many doses have been taken for those patients who sometimes forget if they have taken a previous dose. With solid dosage forms, if a patient has forgotten if a previous dose has been taken, it is often necessary to count the remaining doses to see if one was taken. This creates problems such as contamination and also the likelihood of miscounting wherein the patient might take a double dose or skipped dose due to a counting error. The counter will also keep the user apprized as to when the drug will run out and will help to improve proper planning for the patient to frequent a pharmacy in a timely manner. This can reduce the likelihood of a patient being "surprised" when the system does not provide any unit doses. The device can alternatively count the doses delivered by counting up, or can count down to show the number of unit doses remaining in the system. The counter can be an electrical or mechanical mechanism which are commonly known in the art. The indicator can also be a visual mechanism, e.g., the powder could fall below a colored marker which would indicate the number of doses remaining, the device can expose the internal powder to view in a window, or other mechanisms known in the art.

In the present invention, unlike tablets or capsules which have patient instruction labels on secondary containers, the system of the present invention has a label permanently affixed to the container by the manufacturer, prescriber or dispenser. As the drug is not separated from the container, the label in not disassociated from the drug and the label can be seen at or between each dose.

In certain embodiments, the unit dose of multiparticulates is metered out of the reservoir and expelled from the device. Preferably the unit dose exits the reservoir into a delivery conduit which transports the unit dose out of the device to the oral cavity of the patient or an intermediate receptacle. The delivery conduit can be in the form of a hollow tube, or a molded conduit with a hollow center wherein the unit dose can be transported. In certain embodiments, the unit dose passes through the deliver conduit into the oral cavity due to gravity wherein it is necessary to hold the unit in an upright position during actuation and delivery. However, it is contemplated in certain embodiments of the invention that delivery out of the reservoir and throughout the conduit for delivery of the unit dose can be facilitated by use of a gas or aqueous carrier. For example a gas can be released upon actuation to facilitate the outward motion of the unit dose out of the device. The gas can be pressurized and located in an additional reservoir in the system or it can be compressed in the same reservoir as the multiparticulates. The pressurized gas can be compressed air or liquid gas which becomes a gas upon release from the container. In another embodiment, a liquid can be released from a separate reservoir wherein the multiparticulates and the liquid mix after actuation and a liquid suspension of the multiparticulates is deposited into the oral cavity of the patient.

In preferred embodiments, the system administers the unit dose against gravity by mechanical means. In such an embodiment, the reservoir or blister containing the unit dose is at a point below the mouth prior to administration and upon actuation, the unit dose is moved against gravity to the output cavity, where it is deposited onto the tongue. At the point of deposit, gravity may be used. This provides a more comfortable and convenient motion for the patient, rather than the alternative where the unit dose is at a point higher than the oral cavity and is transported with, or assisted by gravity to the point of output. For example, a sipping straw has a more comfortable and convenient feel to a user when the contents are drawn up to the tongue, rather than drawn down from the point of origin, e.g., the reservoir.

It is also contemplated that the unit dose can be mechanically expelled from the device, e.g., by action of a plunger, auger or similar mechanism. This can be used in order to assure that all of the unit dose is expelled from the device. For example, if there is moisture contamination at the point of expulsion, an amount of the unit dose may stick to the device. A plunger, auger or similar mechanism would minimize or remove this possible situation.

As previously disclosed, it is contemplated that the unit dose may in some circumstances be expelled not into the oral cavity, but into a beverage, food, holder (e.g., a spoon), or other suitable intermediate receptacle prior to ingestion.

DETAILED DESCRIPTION OF CERTAIN EMBODIMENTS

With reference to FIG. 1, a delivery device 1 has a housing 2, which includes a base 3 and an outlet portion 4. Within the housing is a chamber 5 of circular cross section. The chamber encloses a batch 6 of a particulate pharmaceutical preparation, for example, a powder or granular preparation, which comprises an orally active drug. At the upper extremity of chamber 5 is a delivery conduit 7 which communicates with a delivery outlet 8. A cap 9 can cover the outlet 8, and may be attachable by friction fit or snap fit means (not shown in the drawings) to the circumferential surface of the housing 2. A metering device 10 is provided at the periphery of the chamber 5 for the purpose of metering a dose of the preparation from the chamber 5 and discharging the metered dose into the delivery conduit 7. The metering device, which is not shown in FIG. 1, may for example be of a kind used for metering dry powder formulations in dry powder inhalers. One suitable form of such a metering device is described in European Patent Specification No. 0 661 071B, the disclosure of which is incorporated herein by reference.

FIG. 2 shows the device of FIG. 1 in the inverted position. As a result of inversion, the preparation is located immediately adjacent to the delivery conduit 7 and metering device 10. On actuation of the metering device (in the case of devices such as that of EP 0 661 071B, by rotation), a dose of the preparation is metered and discharged into delivery conduit 7, through which it falls under the influence of gravity to delivery outlet 8. If desired, the dispersed dose may be collected in a receptacle 11.

In the use of rotatable metering devices such as those known in the art of dry powder inhalers, it is frequently necessary for the user to employ both his or her hands to use the device, as a result of the twisting action required to actuate the metering device. It is envisaged that the device of the invention might be provided with a gearing means communicating between the rotatable device and a remote actuation device on the device housing, the remote actuation device being arranged to permit actuation using the hand in which the device is held. The remote actuation means may be, for example, operable by pressing or squeezing or a tab or button.

Referring to FIG. 3, in another form of device according to the invention the drug may be delivered directly into the patient's mouth. The device of FIGS. 3 and 4 has an elongate housing 21, in which is mounted a shallow drum-shaped reservoir 22 containing the particulate material 23 to be dispensed. The axis of the reservoir 22 extends transversely across the elongate housing and the reservoir 22 has a diameter that is greater than the width of the housing 21, so that the extremities of the reservoir extend beyond the sides of the housing. The reservoir 22 is rotatable and may be arranged to meter the particulate material 23 in an analogous manner to that described above in relation to FIGS. 1 and 2. A delivery conduit 24 is provided in the housing underneath the reservoir 22 to receive metered doses of material therefrom, for delivery to an opening 25. A mouthpiece 26 is positioned against the housing about the opening 25.

A pathway 27 defined within the mouthpiece 26 communicates with the opening 25 for receiving the particulate material therefrom. An air opening, with a valve (neither is shown) is provided in the housing 21 and also so communicates with the delivery conduit 24 that air can be drawn in through that air opening when a patient sucks through the mouthpiece. The valve is so arranged that it permits only a limited amount of air, in general less than 20 cm3, to be drawn in through the opening during a single sucking action of the patient, the valve closing after that amount of air has passed to prevent further air being drawn in.

The mouthpiece 26 has an elongate portion 28 immediately adjacent to the opening 25. Extending from the elongate portion 28 at the distal end relative to the housing 21 is a flared portion 29 which defines a downwardly facing delivery outlet 30. Underneath the elongate portion 28 is provided a stop member 31 which serves to indicate to the user the correct depth of insertion into the mouth of the mouthpiece 26. The mouthpiece 26 is mounted on a pivot 32, about which the mouthpiece is pivotable from the working position to a storage position. The storage position is indicated in FIG. 3 by broken lines. When the mouthpiece 26 is in the storage position, the opening 25 at the outlet of the delivery conduit 24 may be closed by means of a slidable closure plate 33, which protects against ingress of moisture into the reservoir 22 between dispensing operations. On release of the mouthpiece 26 from the storage position, actuation means (not shown) are operable to actuate the dispensing mechanism (including the reservoir 22) and a dose counter. In FIG. 4, the device is shown with the mouthpiece 26 in the storage position.

The configuration and relative dimensions of the mouthpiece 26 of the device of FIGS. 3 and 4 are chosen so as to ensure that substantially all of the dispersed particulate material 23 is delivered to, and deposited in, the patient's mouth. In particular, they are chosen with the object of preventing accidental inhalation of material. Thus, the elongate portion 28 of the mouthpiece 26 defines a flow channel 27a of relatively small cross-section (for example, of circular cross-section of diameter 5 mm), which at the distal end flares outwardly into a delivery outlet 30 at which the pathway 27b is of much greater cross-section. Furthermore, the delivery outlet 30 is oriented downwardly. The flaring of the distal portion of pathway 27b tends to cause a deceleration of airborne material received from the channel 27a, and that deceleration in combination with the orientation of the outlet 30 promotes the deposit of the material within the patient's mouth and especially on the tongue. In addition, as discussed further below, the particulate material will preferably be so formulated as to minimize the amount of material that will remain airborne on administration, and thus to minimize inhalation.

The device 34 of FIGS. 5 and 6 is similar to that of FIGS. 3 and 4, and parts present in FIGS. 3 and 4 are designated by the same reference numerals in FIGS. 5 and 6. In addition to the structures already described in relation to FIGS. 3 and 4, the device of FIG. 5 contains an additional reservoir 35 with associated metering means (not shown) and associated delivery conduit 36. The delivery conduits 24 and 36 communicate with the pathway 27 in the mouthpiece 26 for delivery of particulate material thereto from respective reservoirs 22 and 35. In FIG. 6, the device of FIG. 5 is shown with the mouthpiece 26 in the storage position. The reservoir 35 will usually contain a particulate material 37 comprising an orally active drug that is different from the orally active drug in the particulate material 23, although it will be appreciated that, if desired, material 37 could contain the same orally active drug, for use as a reserve source or for use in a different dosage. For example, one of the reservoirs may contain a glitazone drug, whilst the other might then contain a sulphonylurea. The choice of further combinations is a matter of routine for those skilled in the art, having regard to the known activities of drugs and any relevant contraindications.

The device 38 of FIG. 7 is in some respects similar to the device 20 of FIGS. 3 and 4, and parts present in FIGS. 3 and 4 are designated by the same reference numerals in FIG. 7. In the case of the device 38, however, there is additionally present a reservoir 39 and metering means (not shown) for a second particulate material 40 comprising a drug for inhalation. The device has a delivery conduit 41, into which material metered from the reservoir 39 enters in use. The delivery conduit communicates with an inhalation airway 42, which is arranged to receive material from the conduit 41. The path from reservoir 22 via delivery conduit 24 into mouthpiece 26 and the path from reservoir 39 via delivery conduit 41 into airway 42 are independent of one another. Whereas, as described in relation to the device 20 of FIGS. 3 and 4, the delivery conduit 24 communicates with an air opening having a valve that limits the intake of air, the delivery conduit 41 communicates with a separate air opening in the housing which permits essentially unrestricted admission of air on inhalation of the patient via airway 42. The device includes selection means (not shown), which are operable by the patient to select which of the materials 23 or 40 is to be administered. According to the selection made by the patient, the air path communicating with the delivery conduit of the non-selected material is closed.

In contrast to the flared outlet 30 of the mouthpiece 26, the airway 42 of device 38 is of substantially constant, or even tapering cross-section and is inclined only slightly downwardly. As a result, the airflow in the airway 42 tends to flow at a relatively high velocity, and possibly even to be accelerated. That, in combination with the orientation of the outlet of the airway, tends to promote inhalation of the particulate material. Suitable combinations of particulate materials for use in the reservoirs 22 and 39 include those comprising any of the orally active drugs already mentioned above (in the case of reservoir 22) and those comprising any drug that is suitable for administration by inhalation (in the case of reservoir 39), provided of course that the selected drugs are compatible in use. Drugs suitable for inhalation will include, but are not limited to, those for use in the treatment or prevention of respiratory disease.

The device of FIG. 7 is especially suitable for administration where there is a need for both a rapid response and for continuing action. For example, in the case of pain control, there is frequently a need for fast relief from pain on commencing treatment, with pain relief then being maintained. A further potential area of use is the treatment of respiratory disease by means of an inhalable drug during the day, and by means of a slower-acting orally active drug for use at night.

Figure 8:
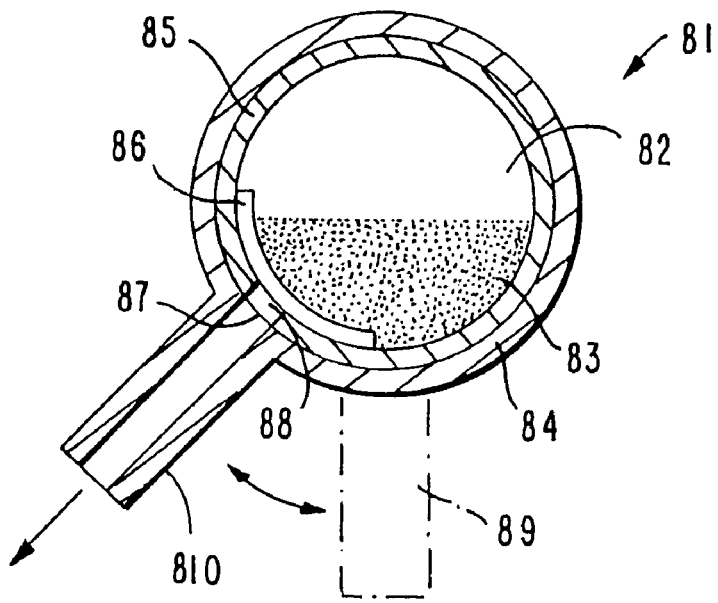
FIG. 8 is an illustration of an embodiment of the invention comprising a drum reservoir.

In certain embodiments as demonstrated in FIG. 8, the system comprises a device which comprises a drum 81 having an inner cavity 82 disposed therein for containing the multiparticulates 83. The drum having an outer lining 84, a rotatable inner lining 85 disposed immediately within the outer lining and a stationary retaining strip 86 located immediately within a portion of the inner lining. The outer lining has a dispensing hole 87 at a point behind the retaining strip to dispense the unit dose and the rotating inner lining has a filling hole 88 disposed therein. The rotating inner lining has a first position 89 where the filling hole is not adjacent to the retaining strip to allow a unit dose of the multiparticulates to be filled therein; and a second position 810 where said filling hole is adjacent to the retaining strip and in communication with the outer hole. Upon actuation, the inner lining is moved from the first position to the second position and the unit dose is delivered from the reservoir to the dispensing hole and expelled from the device for delivery to the patient. In this embodiment, the drum which holds the multiparticulates can be spherical or cylindrical.

Figure 9:
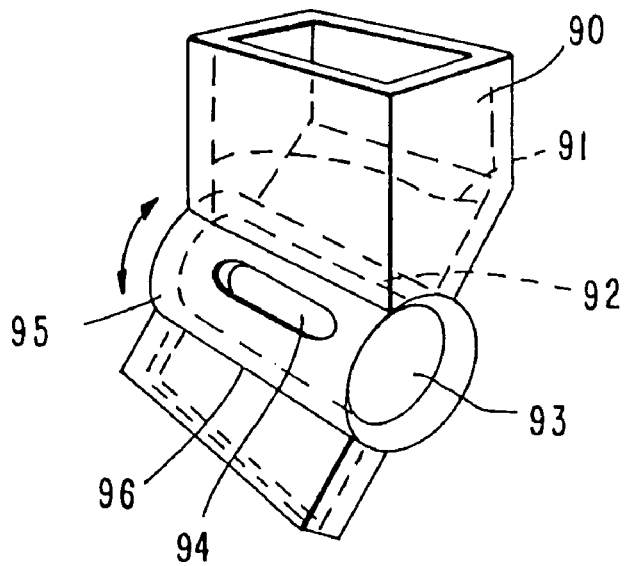
FIG. 9 is an illustration of an embodiment of the invention having a rotatable member outside of the reservoir.

In another embodiment as demonstrated in FIG. 9, the system comprises a device which comprises a reservoir 90 containing the multiparticulates 91 which has an exit hole therein 92; a rotatable member 93 outside the reservoir having an external cavity 94 in communication with the exit hole when the rotatable member is in a first position, to allow a unit dose of the multiparticulates to be filled therein; a stationary retaining housing 95 immediately covering the rotating member, the retaining housing having a dispensing hole 96 disposed therein; the rotatable member having a second position wherein the external cavity of the rotatable member is in communication with the dispensing hole wherein upon actuation, the rotatable member is moved from the first position to the second position whereby the unit dose is delivered from the reservoir to the dispensing hole and expelled from the device for delivery to the patient.

Figure 10:
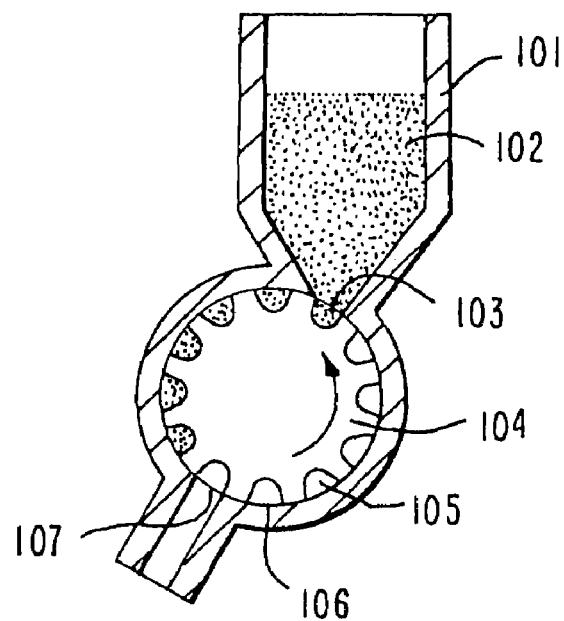
FIG. 10 is an illustration of is an illustration of an embodiment of the invention having a rotatable wheel outside of the reservoir.

In another embodiment as demonstrated in FIG. 10, the system comprises a device which comprises a reservoir 101 to contain the multiparticulates 102, the reservoir having an exit hole 103 therein; a rotatable member 104 outside the reservoir having a plurality of external cavities 105; a stationary retaining housing 106 immediately covering the rotating member, the retaining housing having a dispensing hole 107 disposed therein; the rotatable member in position wherein one external cavity is in communication with the exit hole, to be filled with a unit dose of the multiparticulates and one external cavity is in communication with the dispensing hole; the rotating member being rotatable to advance each cavity to the exact position of the next adjacent cavity wherein a unit dose of the multiparticulates is delivered from the dispensing hole when a cavity containing a unit dose is advanced to be in communication with the dispensing hole.

Figure 11:
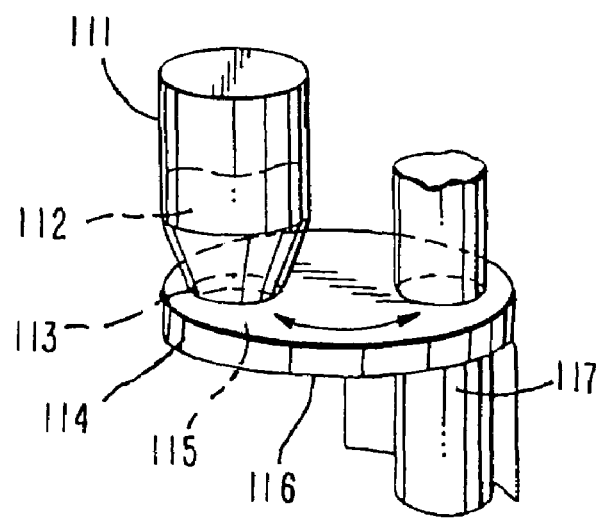
FIG. 11 is an illustration of an embodiment of the invention having a rotatable plate mechanism.
Figure 12:
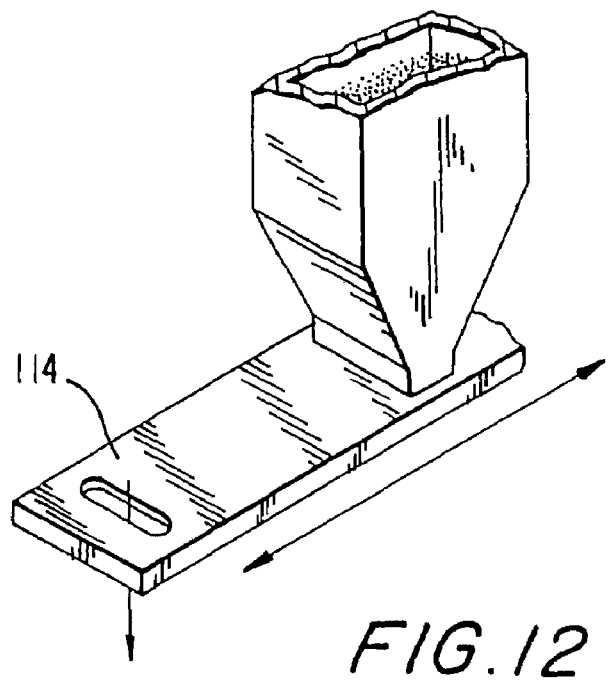
FIG. 12 is an illustration of an embodiment of the invention having a slidable plate mechanism.
Figure 13:
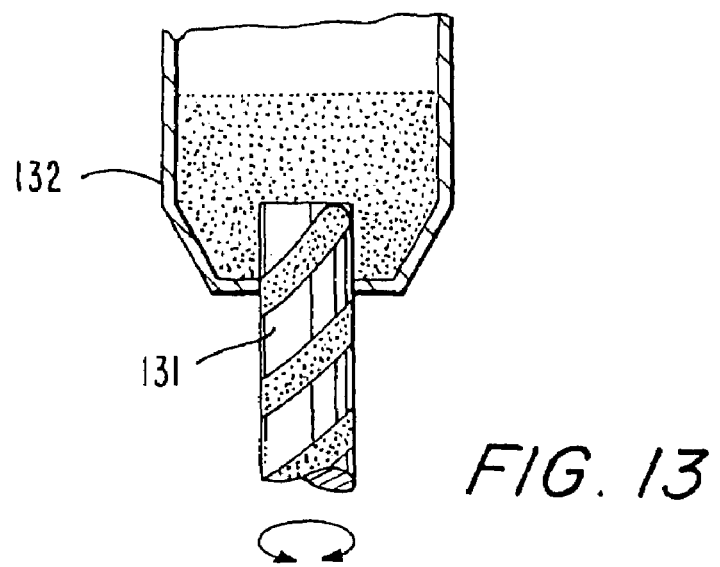
FIG. 13 is an illustration of an embodiment of the invention having an archimedean screw.

In another embodiment as demonstrated in FIG. 11, the system comprises a device which comprises a reservoir 111 to contain the multiparticulates 112, the reservoir having an exit hole 113 therein; a movable plate 114 having a filling hole 115 disposed therein, the movable plate having a first position wherein the filling hole is in communication with the exit hole of the reservoir; a stationary retaining plate 116 immediately under the movable plate to form a filling cavity with the filling hole, to be filled with a unit dose of multiparticulates when the movable plate is in the first position, the stationary retaining plate having a dispensing hole 117; the movable plate having a second position wherein the filling hole is in communication with the dispensing hole. Upon actuation, the moving plate moves from the first position to the second position and a unit dose is delivered from the reservoir to the dispensing hole, where it is expelled from the device and administered to the patient. In an alternate embodiment, the device has a stationary upper plate immediately over the movable plate, the upper plate having a hole therein in communication with the reservoir hole and the filling hole in order to retain the unit dose in the cavity during transmission from the first to the second hole. In certain embodiments, as shown in FIG. 11, the movable plate 114 is circular and rotatably moves from the first position to the second position. In other embodiments as demonstrated in FIG. 12, the movable plate 114 is rectangular and slidably moves from the first position to the second position.

In another embodiment of the invention, the system comprises a device comprising an archimedean screw 131 capable of reciprocal movement to dispense a unit dose of multiparticulates from the reservoir 132 to be discharged from the device into the oral cavity of the patient.

Figure 14:
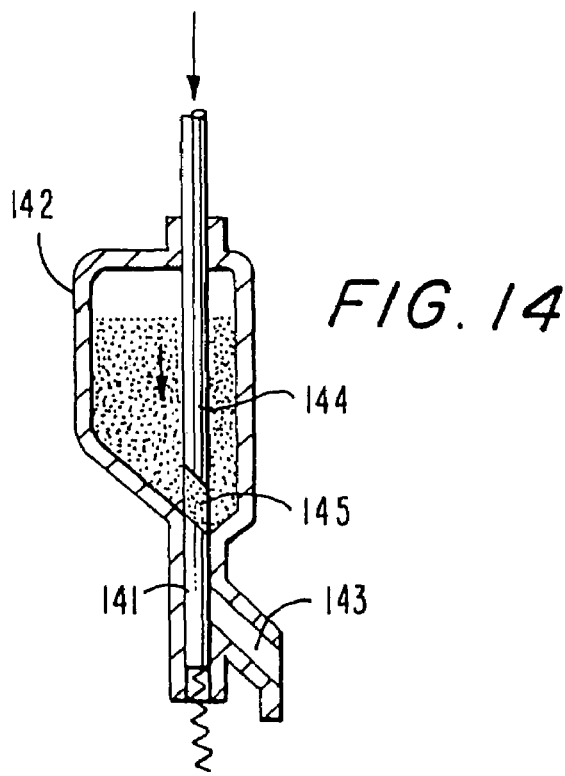
FIG. 14 is an illustration of an embodiment of the invention having a slidable member mechanism.
Figure 15:
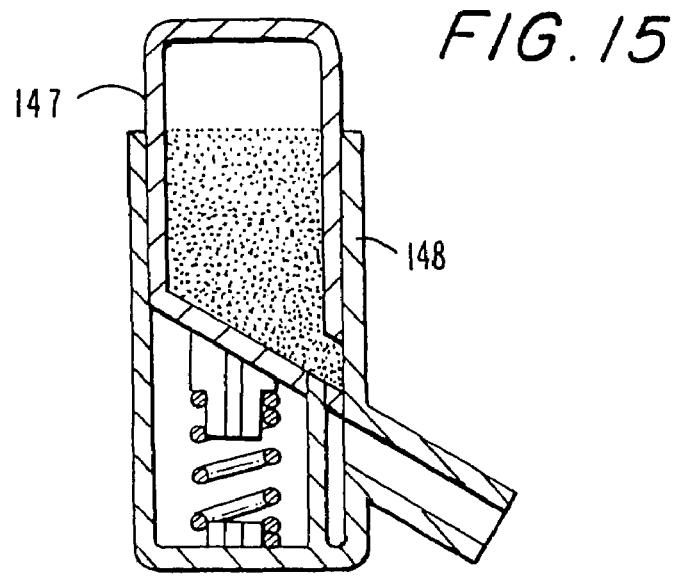
FIG. 15 is an illustration of an embodiment of the invention having a slidable reservoir mechanism.

In another embodiment of the invention as demonstrated in FIG. 14, the system comprises a device comprising a shaft 141 in communication with a reservoir 142 and a delivery conduit 143 in communication with the shaft, wherein said device is capable of providing a unit dose of the drug from the reservoir to the delivery conduit. In a certain embodiments, the device further comprises a slidable member 144 within the reservoir and the shaft, the slidable member having a filling cavity 145 disposed therein, the slidable member having a first position with the filling cavity located in the reservoir and a second position with the filling cavity located in the shaft and in communication with the delivery outlet. Upon actuation, the slidable member moves from the first position to the second position, and a unit dose of the drug is discharged from the reservoir into the delivery conduit and subsequently into the oral cavity of the patient. In preferred embodiments, a mechanism, e.g. a spring., 146 returns the slidable member to the first position after release of the unit dose. In an alternate embodiment as demonstrated in FIG. 15, the slidable member is the reservoir 147 which is enclosed within a housing 148.

Figure 16:
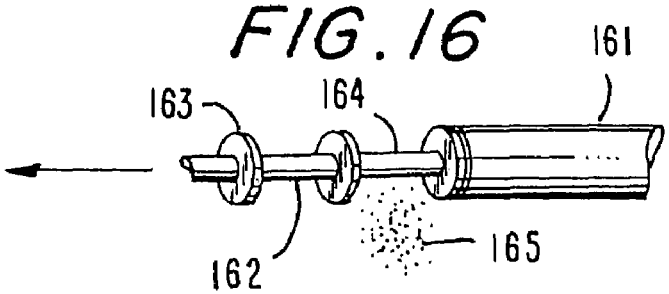
FIG. 16 is an illustration of an embodiment of the invention having a pull cord mechanism.

In another embodiment of the invention as demonstrated in FIG. 16, the system comprises a device comprising an elongated tube 161 having an internal cord 162, the cord having a plurality of evenly spaced nodules 163 which plug the tube to form a plurality of evenly spaced air pockets 164 within the tube, each of which contains a unit dose of the multiparticulates 165; wherein upon actuation, the cord is pulled to expose a single air pocket and the unit dose is dispensed from the system and subsequently dispensed to the oral cavity of the patient.

Figure 17:
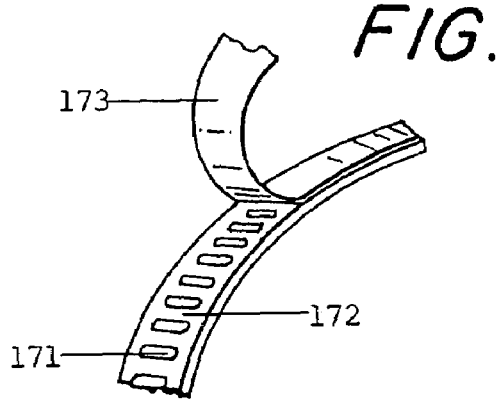
FIG. 17 is an illustration of a blister pack.
Figure 18:
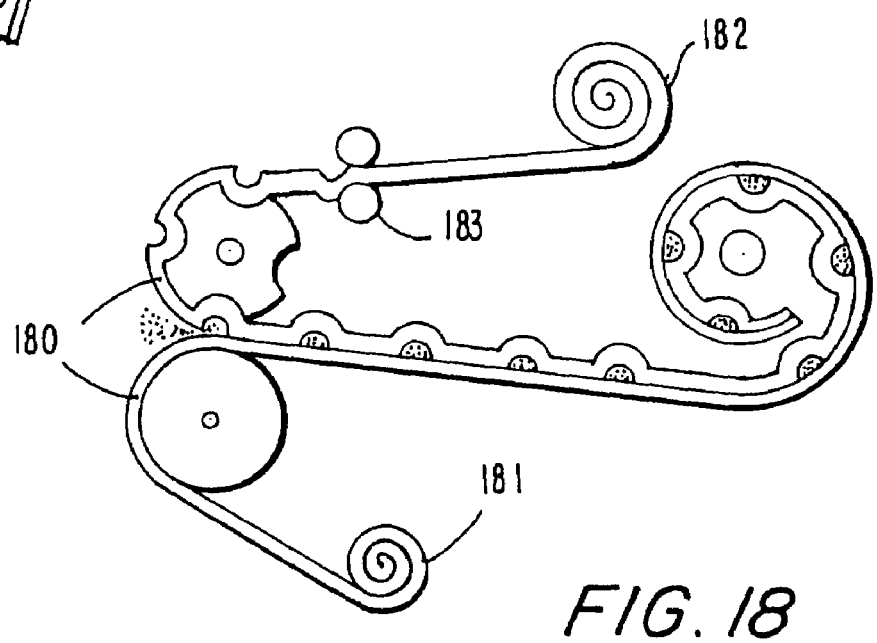
FIG. 18 is an illustration of an opening mechanism for a blister strip or roll

In certain embodiments of the invention, the unit doses are individually metered prior to actuation. FIG. 17 illustrates an embodiment comprising unit doses contained in blisters 171 on a substrate base 172, each blister containing a unit dose, the substrate base and the blisters covered by a seal 173. In certain embodiments the blisters are aligned linearly in the form of a strip, and in alternate embodiments, the strip is in the form of a roll In certain embodiments of the system comprising premetered blisters as demonstrated by FIG. 18, upon actuation, the blister strip or roll is advanced by a gear mechanism 180, an amount of seal covering one blister is taken up by a first take up roller 181 and an equal portion of substrate base is taken up by a second take up roller 182, whereby a unit dose of multiparticulates is expelled from the strip and dispensed from the system into the oral cavity of the patient. Preferably, pinch rollers 183 are utilized in order to straighten the substrate base to facilitate the rolling and storage of the used blister substrate.

Figure 19:
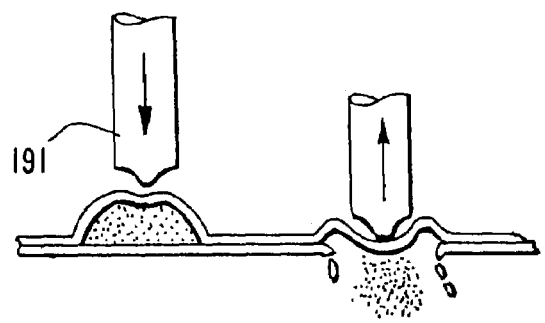
FIG. 19 is an illustration of a piercing mechanism for a blister strip or roll.

In other embodiments of the system comprising premetered blisters as demonstrated by FIG. 19, the system further comprises a piercing member 191, wherein the strip is advanced to have a blister aligned with the piercing member wherein upon actuation, the piercing member penetrates the blister and a unit dose of multiparticulates is expelled from the strip and dispensed from the system into the oral cavity of the patient.

Figure 20:
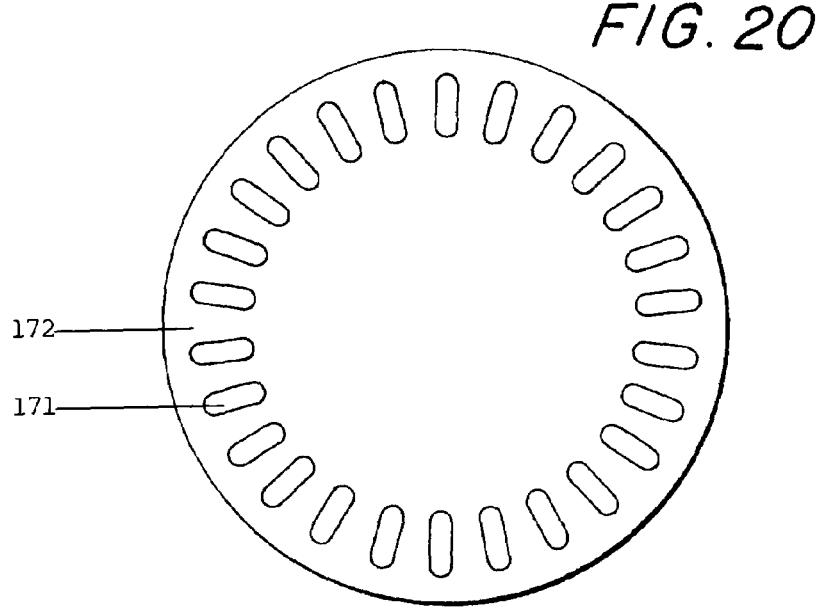
FIGS. 20 and 20A are illustrations of circular blister packs.
Figure 20A:
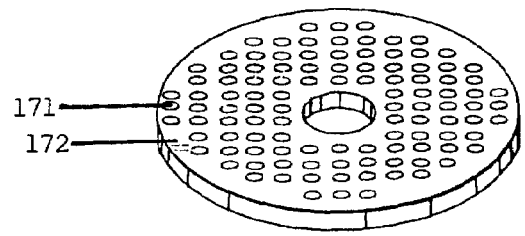
Figure 21E:
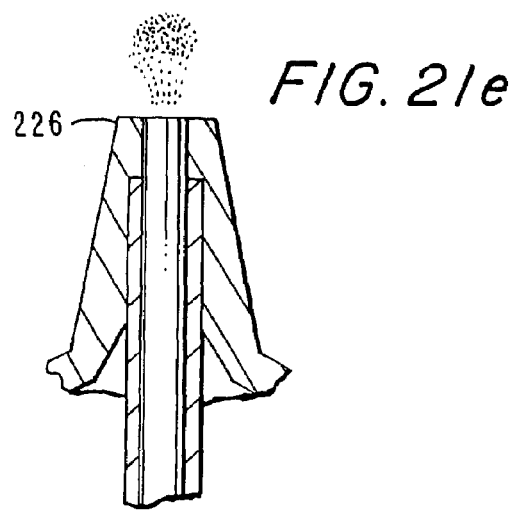
FIG. 21 is an illustration of a powder delivery device comprising a lifting rod.
Figure 21F:
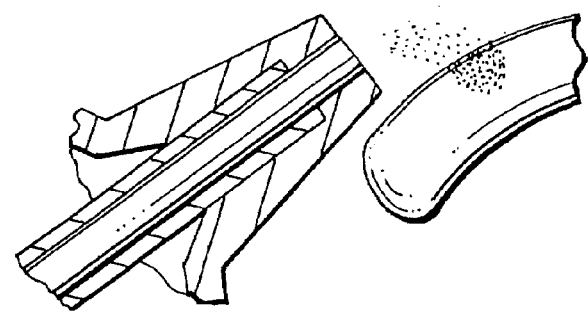
Figure 21G:
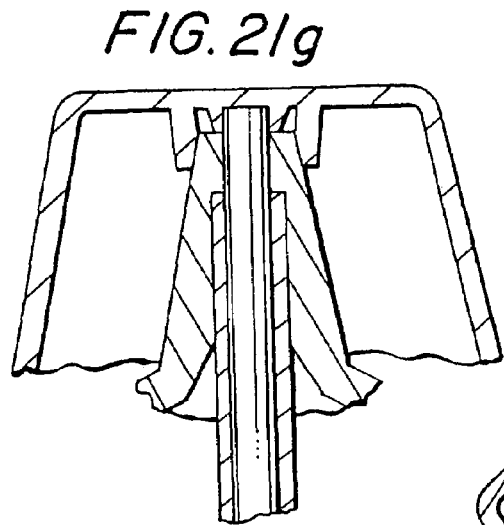
Figure 21H:
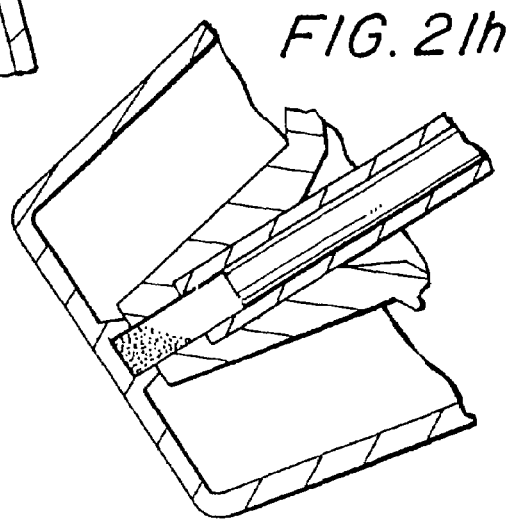
Figure 21I:
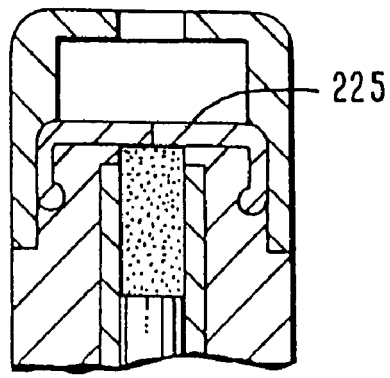
Figure 21J:
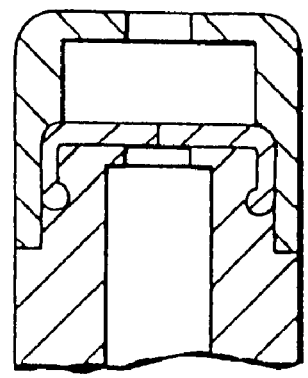
Figure 21K:
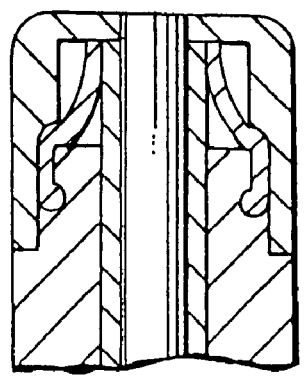
Figure 21L:
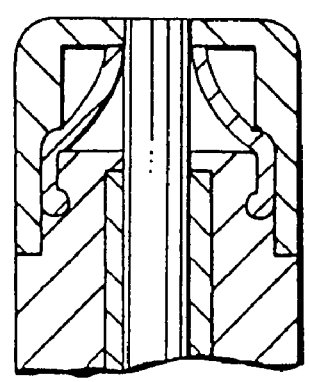
Figure 22H:
FIG. 22 is an illustration of a powder delivery device with an optionally coupled powder feeder.
Figure 22I:
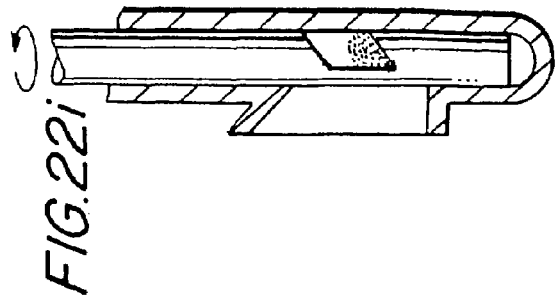
Figure 22C:
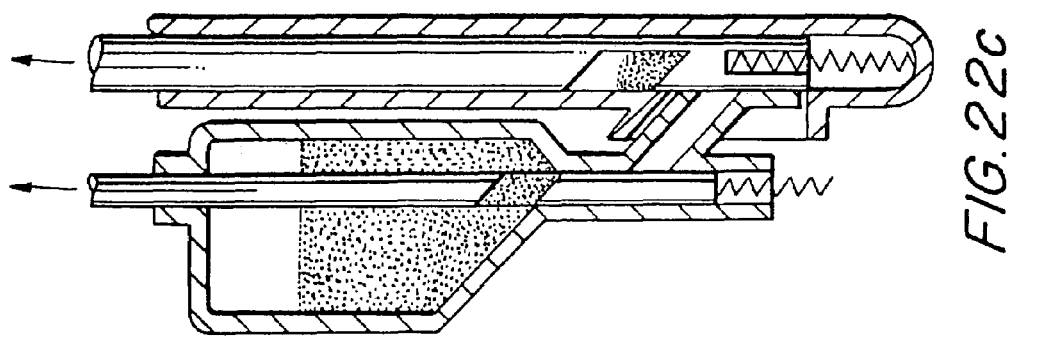
Figure 22B:
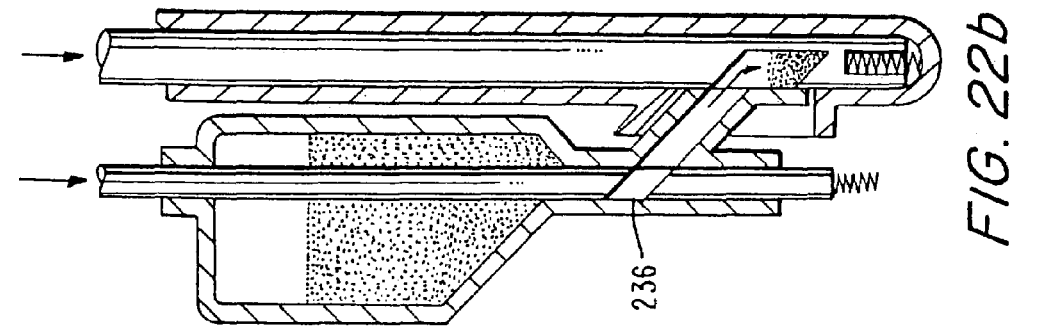
Figure 22A:
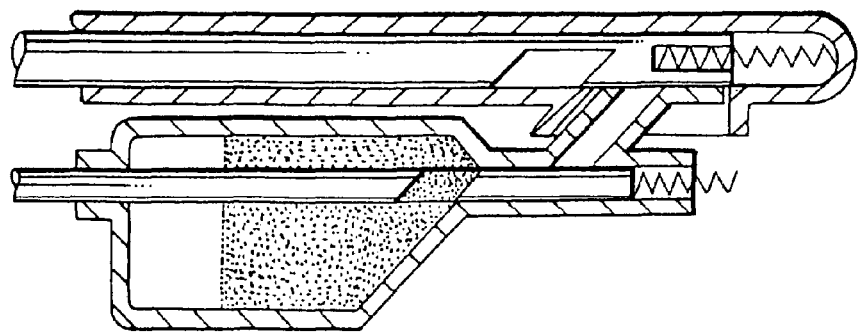

In embodiments of the system comprising premetered blisters, the substrate base is disk shaped with the blisters arraigned on the periphery of the disk. The blisters being equidistant from each other and from the center of the pack as demonstrated by FIG. 20, wherein upon actuation the substrate base rotates about its central axis and positions a blister in alignment with a piercing member. The piercing member penetrating the blister to expel the unit dose from the blister to be dispensed from the system into the oral cavity of the patient. In alternate embodiments, the blisters can be arranged as a matrix as demonstrated by Fog. 20*a*, which would require a more complex mechanism in order to advance the blisters to te piercing member, or vice versa.

Another embodiment of the invention as demonstrated in FIG. 21 is directed to a device for depositing a unit dose of multiparticulates comprising a drug to the tongue of a patient comprising a housing 211 having an inner cavity 212 formed therein for containing multiple doses of the multiparticulates 213, the housing having a tapered top end 214 with an opening therein 215 and a tapered bottom end 216; a lifting rod 217 fitted at a first position 218 within the tapered bottom end of the housing which is movable to a second position 219 within the tapered top end of the housing, the lifting rod comprising an elongated cylinder 220 with a top end 221 and an inner push rod 222 within the elongated cylinder which terminates at a point below the top end of the cylinder to form a filling cavity 223 when the lifting rod is in the first position (b), the inner push rod movable to terminate at a point above the top end of the cylinder when the lifting rod is at the second position (d); wherein when the device is upright in the first position, the filling cavity is filled with a unit dose of the multiparticulates and when the lifting rod is moved to the second position, the inner push rod moves to a point above the top end of the cylinder and the unit dose of drug is expelled from the housing onto the tongue of the patient (f). This embodiment of the invention can further comprising an endcap 224 covering the opening of the tapered top end or at least one shutter 225 covering the opening of the tapered top end, wherein the at least one shutter opens when the lifting rod is in the second position. This embodiment of the invention can further comprise an inner ridge 226 in the opening of the tapered top end, the inner ridge configured to engage and stop the motion of the elongated cylinder and not the inner push rod, allowing the inner push rod to terminate at a point above the top end of the cylinder to expel the unit dose. The placement of the inner push rod in the elongated cylinder at the first position is preferably adjustable in order to vary the volume of the filling cavity and individualize the dose of the drug. Preferably, the top tapered end is of sufficient length to allow the dose to deposit onto the back of the tongue of the patient. In certain embodiments, the device can be loaded with drug and cocked at a position between the first and second position prior to actuation as demonstrated in (c).

Another embodiment of the invention as demonstrated by FIG. 22 is directed to a device for depositing a drug onto the tongue of a patient comprising an elongated housing 221 having an inner cavity 223, the housing having an opening 224.1 connecting the inner cavity to outside of the housing, the housing adapted to fit within the oral cavity of a human patient with the opening facing the tongue of the patient; a movable member 225.1 within the inner cavity, the movable member having a filling aperture 226.1 capable of containing a dose of drug, the filling aperture enclosed by the housing when the movable member is in a first position (e), the movable member capable of being positioned to a second position (f) wherein the filling aperture is in communication with the housing opening to load the drug into the aperture or to discharge the drug onto the tongue of the patient. In certain embodiments, the movable member is horizontally slidable from the first position to the second position or is rotatable within the elongated housing and rotates from the first position to the second position (h, i). Preferably, the elongated housing is of sufficient length to allow the drug to deposit on the back of the tongue of the patient. This embodiment can also comprise a powder feeder 227 coupled to the opening of the housing to deposit a unit dose of drug into the aperture when the movable member is in the second position, the powder feeder being completely removable from the housing in order to allow for the deposit of the dose onto the tongue of the patient. In preferred embodiments, the powder feeder is attached to the housing by a folding member (e.g. a hinge, spring, flexible strip or similar mechanism) which provides a closed position and an open position. When the housing and the powder feeder are in the closed position, the powder feeder is coupled to the opening of the housing and is in position to deposit a unit dose of drug into the filling aperture 226 with the movable member is in the second position. In the open position, the housing and the powder feeder are in a spatial relationship which allows the housing to dispense the unit dose into the mouth of the user without hindrance due to the presence of the powder feeder. In order to reduce steps involved in dispensing the drug, the folding action from the open position to the closed position, or vice versa, can actuate a step in the dispensing process. For example, the opening of the device could trigger the filling of the aperture and/or the movement of the movable member from the second position to the first position. Alternatively, the opening of the device could trigger the filling of the aperture, the movement of the movable member from the second position to the first position during the initial opening, and the movement of the movable member back to the first position for dispensing, during the end of the opening action, when the subsequent dispensing is unhindered by the powder feeder. The powder feeder can comprise any mechanism for metering powder, including any of the above disclosed reservoir systems, e.g., the powder feeder can comprise a housing 228 forming an inner reservoir 229 to hold multiple doses of the drug in powder form 230, a shaft 231 in communicating with the reservoir and a delivery outlet 232 in communication with the shaft, wherein the powder feeder is capable of providing a unit dose of the drug from the reservoir to the delivery outlet. In one embodiment, the powder feeder further comprises a slidable member 233 within the inner reservoir and the shaft having a filling cavity 234 disposed therein, the slidable member having a first position 235 with the filling cavity located in the reservoir and a second position 236 with the filling cavity located in the shaft and in communication with the delivery outlet, wherein upon movement of the slidable member from the first position to the second position, a unit dose of the drug is discharged from the powder feeder into the filling aperture of the movable member.

Another embodiment of the invention as demonstrated by FIG. 23 is directed to a device for depositing a drug onto the tongue of a patient comprising a housing 231 forming a reservoir 232 and a shaft 233 in communication with the reservoir, the housing having an opening 234 connecting the shaft to outside of the housing, the housing adapted to fit within the oral cavity of a human patient with the opening facing the tongue of the patient; a movable member 235 having a filling aperture 236 capable of containing a dose of drug, the movable member fitted within the shaft in a first position (b) wherein the filling aperture is in communication with the reservoir and capable of being filled with the dose, the movable member capable of being positioned to a second position (d) with the filling aperture in communication with the housing opening wherein the dose of drug is discharged onto the tongue of the patient. In certain embodiments the movable member is horizontally slidable from the first position to the second position or is rotatable within the elongated housing and rotates from the first position to the second position. The device can further comprise a locking mechanism 237 to keep the position of the filling aperture at a location between the first and second position (c). Preferably, the device comprises a mechanism, e.g. a spring 238, to position the movable member to the second position upon release of the locking mechanism. Preferably, the top tapered end is of sufficient length to allow the dose to deposit onto the back of the tongue of the patient and has a removable cap 239.

The systems and device of the present invention should contain the powder in order to prevent contamination from the outside environment as well as to assure a closure o prevent loss and waste of powder. This can be accomplished by elastomeric sealing gaskets which can provide a seal between the reservoir and the other components to prevent leakage or escape of powder from the reservoir. Alternatively, this can be accomplished by biasing the components with, e.g. a screw, in order to provide tight frictional engagement between the drug containing components.

Another aspect of the invention is directed to novel mouthpieces which aid in the coordination of the unit dose into the oral cavity.

Figure 24:
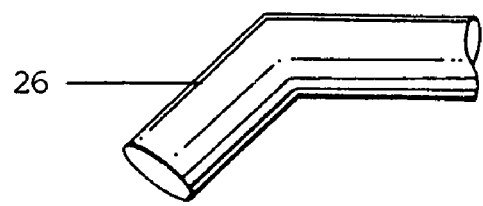
FIG. 24 is an illustration of an angled mouthpiece.
Figure 25:
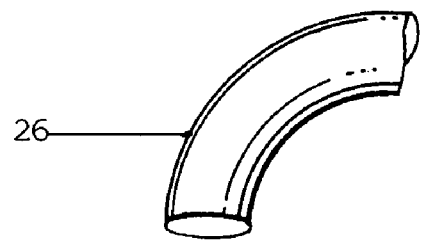
FIG. 25 is an illustration of a curved mouthpiece.

In certain embodiments, the mouthpiece initially protrudes from the device in a similar manner as a traditional mouthpiece on a standard inhaler. However, after the initial protrusion, the mouthpiece angles downward in order to direct the unit dose onto the tongue of the user as shown in FIG. 24. This is to assure that as close to 100% as possible of the unit dose is subsequently absorbed by the gastrointestinal tract and not inhaled into the pulmonary system. The angled mouthpiece can have a sharp angle (FIG. 24) or can be curved as shown in FIG. 25.

Figure 26:
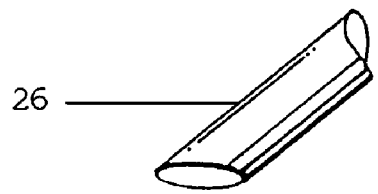
FIG. 26 is an illustration of a straight angled mouthpiece.

In another embodiment, rather than having the angled or curved mouthpiece, the mouthpiece can be straight, but can protrude from the device, when the device is in an upright position at an angle (FIG. 26) in order to direct the unit dose onto the tongue and also to reduce any deflection in the mouthpiece from the angle and curved mouthpiece which may result in some drug being retained and not delivered by the system.

Figure 27:
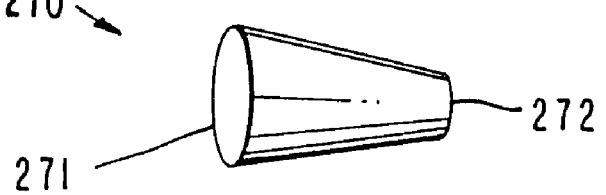
FIG. 27 is an illustration of a conical mouthpiece.

Another novel feature of the mouthpiece of the present invention is to have a flared mouthpiece which reduces the velocity of the multiparticulates and prevents the scattering and dispersion of the dose which may lead to pulmonary infiltration. In the prior art, narrowed or venturi style mouthpieces result in an increased velocity during delivery which is beneficial for pulmonary inhalation. By virtue of the flared mouthpiece of the present invention, the velocity of the multiparticulates is not increased, thereby increasing the percent of drug deposited gastrointestinally. As shown in FIG. 27, the flared mouthpiece can be conical in shape 270, wherein diameter of the outlet of the mouthpiece 271 is large than the internal entrance 272 wherein the unit enters the mouthpiece. In preferred embodiments, the outlet diameter is 25%, 50% or 100% greater than the inlet diameter of the mouthpiece. However these percentages are not meant to be limiting.

Figure 28:
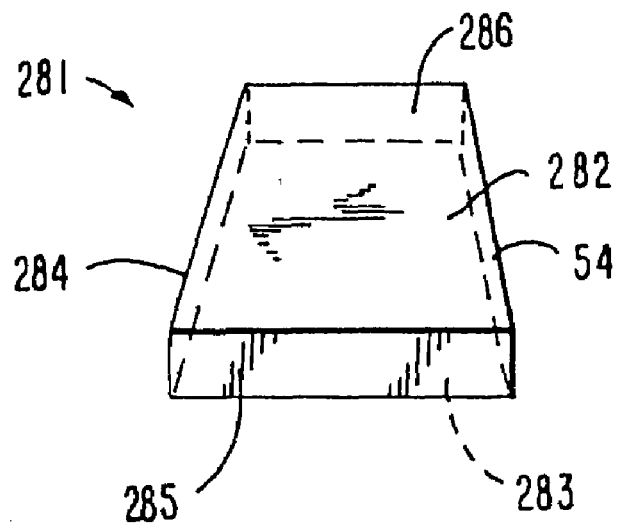
FIG. 28 is an illustration of a rectangular mouthpiece.

In other embodiments as demonstrated in FIG. 28, the mouthpiece can be rectangular 281, with the horizontal top 282 and bottom 283 being longer than the sides 284 in order to fit within the mouth of a patient. Similarly to the conical mouthpiece the outlet of the opening 285 will be greater than the inlet opening 286. For example, the surface area of the outlet opening van be 25%, 50% or 100% larger than the inlet opening.

Figure 29:
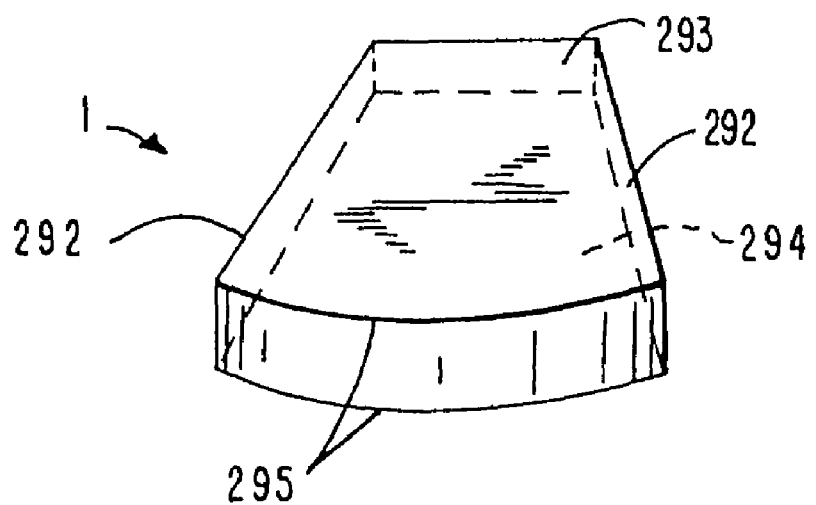
FIG. 29 is an illustration of a fanlike rectangular mouthpiece.

In other embodiments with a rectangular style mouthpiece as depicted in FIG. 29, the outward protrusion of the mouthpiece 291 can be fanlike. In such an embodiment the side walls 292 of the mouthpiece extend outward from the beginning of the mouthpiece 293 as angles, e.g. 15 degrees, going in opposite direction from each other to provide the flare. When the walls reach the desired distance, the top and bottom of the mouthpiece 294 are convex on their outer edges 295 in order to provide the fanlike appearance.

In certain embodiments of the invention, drug delivery devices known in the art, e.g., powder inhaler art, can be modified/adapted in order to have the capacity and the capability to actuate a unit dose of particles having a size suitable for gastrointestinal delivery with minimal inhalation into the pulmonary system. Such devices are described in the above mentioned WO 94/04133, U.S. Pat. No. 4,590,206 and WO 93/25198, hereby incorporated by reference. Other devices are described below:

One such device is known as the Bespak device described in PCT publication WO 92/00771, hereby incorporated by reference, available from Innovata Biomed Limited. The device described therein includes a storage chamber for storing a powdered drug to be administered and a metering member having metering cups in which individual doses of the powdered drug are placed. Air is inhaled through an inhalation passage at one end of the device and directed into contact with the metering cup that has been filled with the powdered drug. The metering cup is oriented upwardly open to face the air stream and to enable the powder to be released from the cup. Upon inhalation, the dose is mixed with the air flow and continues through the mouthpiece to be inhaled. The metering cups on the metering member are arranged on an outer frusto-conical wall so that each metering cup is positioned to be upwardly open and face the air flow during inhalation. The metering member rotates so that the metering cups move between a position in which the cup receives a dose of the powered drug from the storage chamber to a position in which the cup is exposed to the air flow. As one cup is exposed to the air flow, another cup is aligned with the storage chamber and is being filled with powder. After the dose is blown from the metering cup, and upon subsequent rotation of the metering member, the cup is wiped and cleaned by a wiping element to remove any undispersed powder and then dried via a moisture absorbent material.

Another device for delivery of inhalation powders is described in U.S. Pat. No. 2,587,215 (Priestly), hereby incorporated by reference. Priestly describes an inhaler having a storage chamber containing a powdered drug, a mixing chamber and means to move a set dose of drug from the storage chamber to the mixing chamber. The dose is mixed with air in the mixing chamber and inhaled through a mouthpiece.

Yet another inhalation device suitable for delivering powdered inhalation drugs is described in U.S. Pat. No. 4,274, 403 (Struve), hereby incorporated by reference. Struve describes an inhaler for administering a powdered drug nasally, which includes storage means for containing a quantity of the drug therein. The storage means includes a feed hole through which the powdered drug may be received from the storage means. The device further includes a dispensing head operatively coupled to the storage means for dispensing the powdered drug more nasally. The dispensing head of the Struve inhaler includes a nozzle, a body portion, a dispensing cylinder and a vent means. The nozzle is shaped to be received in the nasal passage of the user. The nozzle includes a dispensing passageway for dispensing the dose into the nasal cavity of patient. The body portion is located adjacent the nozzle and has a traverse bore therein. The traverse bore operatively connects the dispensing passageway in the nozzle with the feed hole leading to the drug storage means. The feed hole and the dispensing passageway are transversely offset relative to one another at the points where they enter the transverse bore.

The dispensing cylinder includes a metering chamber. The metering chamber may be selectively aligned with either the feed hole or the dispensing passageway. The dispensing cylinder is slidably received in the transverse bore for movement between a first transverse position in which the metering chamber is aligned with the feed hole and a second transverse position in which the metering chamber is aligned with the dispensing passageway. In its first position, the metering chamber can be filled with a charge of the powdered drug when the inhaler is manipulated. In the second position, places the charge of the powdered drug into the dispensing passageway for inhalation by the user. The vent means is formed as part of the dispensing cylinder and is capable of venting the metering chamber to atmosphere only in the second position of the cylinder, i.e. when the powder disposed in the device such that it may be inhaled by the user.

Another inhaler device is disclosed in U.S. Pat. No. 4,524,769 (Wetterlin), hereby incorporated by reference. Wetterlin describes a dosage inhaler for administering a micronized pharmacologically active substance to a patient. The inhaler includes a gas conduit means through which gas passes for carrying the micronized substance to be administered. The inhaler further includes a membrane having a plurality of preselected perforated portions, each portion adapted to hold and dispense a reproducible unit dose of less than 50 mg of said active substance, in dry powder form. The powder particles have a particle size of less than 5 micrometers. The membrane is movably connected to the gas conduit means so that one of the preselected portions can be positioned within the gas conduit means so that the substance held in the preselected portion may be dispensed. The remaining preselected portion can be in a position external to said gas conduit means to receive said active substance. The membrane is movable through a plurality of positions whereby each preselected portion of the membrane can be successively positioned within the gas conduit to dispense the unit dose of the active substance held therein. Each preselected portion from which the active substance has been dispensed can be moved to said external position to receive active substance.

GB Patent Application No. 2,041,763, hereby incorporated by reference, describes an inhaler having a powder storage chamber and a rotatable metering member having dosing holes which open to the storage chamber in one position and open to the mixing chamber in another position. Upon rotation of the metering member, the powder is carried from the storage chamber to the mixing chamber to be inhaled.

EP 0 079 478, hereby incorporated by reference, describes an inhaler having a storage chamber, inhalation air passage and rotatable delivery member having a cavity formed therein. The delivery member is rotated from one position in which the cavity receives powder from the storage chamber to another position in which the powder falls from the cavity by the effect of gravity into a collector positioned in the air passage.

U.S. Pat. No. 4,860,740 (Kirk et al.), hereby incorporated by reference, describes an inhaler having a rotatable metering member with recesses formed therein. The recesses contain a powdered drug. Upon rotation of the metering member, one of the recesses in exposed to the air inhalation passage to be entrained in the air stream and inhaled.

The Easyhaler.™., described in PCT publication WO 92/09322, hereby incorporated by reference, available from Boehringer Ingelheim is illustrative of another suitable device which can be adapted/modified for delivering the formulations of the present invention. The device includes a supply of a pulverized medical substance and a "dosing means", which is a rotatable cylinder having five uniform recesses arranged around the periphery of the cylinder. The cylinder is rotated such that one recess aligns with the supply of drug and is filled by a quantity of the drug while another recess aligns with an air channel connected to the mouthpiece. The filled recess is then rotated to another position in the direct path of an inhalation air flow. The dose is pre-set by the recessed portion of the rotatable dosing means and is flushed clean by the direct air flow through the inhalation chamber. To operate the device, the rotating dosing means is turned so that a full dosing chamber (having already been filled up after the previous use) is rotated into alignment with the air channel leading to the mouthpiece. Upon inhalation by the user, air is drawn through apertures and nozzles directly into the dosing chamber. The air flow flushes the dosing chamber causing the drug to be carried with the air in the direction of the inhalation through the mouthpiece. The axis of the air channel is arranged at an angle to the axis of the dosing means of between 70.degree. and 110.degree., but preferably 90.degree. (perpendicular).

U.S. Pat. No. 5,176,132, hereby incorporated by reference, discloses a device for the administration to the lung by inhalation of a drug in powdered form. The device includes a mouthpiece, a drug reservoir communicating with said mouthpiece, and metering means for dispensing a dose of drug from the reservoir. The reservoir contains a compacted body of powdered drug including an active ingredient having a particle size of from 1 to 10 μm when in loose powder form. The metering means includes a rotatable helical blade for abrading the compacted body. Thus when actuated, the helical blade abrades the compacted powdered drug into particles capable of being inhaled into the respiratory tract of a patient.

International patent applications, PCT/EP93/01157 and PCT/EP93/01158 (assigned to GGU), hereby incorporated by reference, are directed to an inhalation device and to a annular tablet, respectively. GGU's device includes a drug reservoir body situated in a mouthpiece. The body forms the beginning of an inhalation tube through which the drug is inhaled. The drug is in a compacted and annular (ring) form. In use, a face mill cutter rotates, generating particles of the drug. Upon inhalation, air flows through air inlet openings in the casing and in the area of the cutting edges of the face mill cutter. Together with depressions situated between the cutting edges, the inlet openings and the depressions form an air channel leading to the mouthpiece, through which the drug particles are inhaled.

The quantity of each dose is determined by the amount of rotations of the face mill cutter. A spring presses the inhalation tube and thus the drug body toward the face mill cutter. In operation, a wind-up button is rotated to load the spring. By pressing the trigger mechanism, the spring is released thereby rotating the upper portion to which is connected the face mill cutter.

Other representative inhalers for medications are those described in, for example, U.S. Pat. Nos. 3,157,179; 3,178,748; 3,183,907; 3,356,088; 3,361,306; 3,456,644; 3,456,646; 3,565,070; 3,656,070; 3,636,949; 3,658,059; 3,732,864; 3,789,843; 3,814,297; 3,991,761; 3,826,413; 4,206,758; 4,414,972; 4,484,577; 4,534,345; 4,592,348; 4,817,822; 4,484,577; 4,926,852; 4,790,305; 4,210,155; 4,852,561; 4,644,107; 4,677,975; 4,803,978; 4,934,358; 4,955,371; 5,020,527; 5,048,514; 5,060,643; 5,224,471; 5,250,287; 5,284,133; and 5,351,683. Representative of nasal-pharyngeal inhalers for large mammals such as a horse is that described in U.S. Pat. No. 5,062,423.

Representative devices for handling powder forms of medicine are shown and described in several U.S. Patents, including U.S. Pat. Nos. 6,142,146; 6,116,238; 6,073,818; 6,071,498; 6,065,471; 6,029,663; 6,006,747; 5,934,273; 5,875,776; 5,871,010; 5,785,049; 5,577,497; 5,694,920; 5,642,728; 5,568,807; 5,546,932; 5,524,613; 5,476,093; 5,447,151; 5,383,850; 5,372,128; 5,301,666; 5,287,850; 5,263,475; 5,042,472; 4,889,114; 4,860,740; 4,846,168; 4,338,931; 5,458,1351; 5,388,572; 5,349,947; 5,042,472; 3,507,277; 3,518,992; 3,635,219; 3,831,606; 3,948,264; 3,971,377; and 4,147,166. Dry powder inhalers include dose inhalers, for example the single dose inhaler known by the trade mark Monohaler® and multi-dose inhalers, for example a multi-dose, breath-actuated dry powder inhaler such as the inhaler known by the trade mark Turbohaler®. Many of these prior art devices use powdered medicine contained in a gelatin capsule or blister with a separate dose contained in each capsule or blister. For example, in U.S. Pat. Nos. 3,507,277; 3,518,992; 3,635,219; 3,795,244; and 3,807,400, inhalation devices are described having means for piercing of a capsule containing a powdered drug, which upon inhalation is drawn out of the pierced capsule and into the user's mouth. In U.S. Pat. No. 2,517,482, a device is described having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. One well known dry powder inhaler, the Diskhaler, described in U.S. Pat. No. 4,627,432, uses individual drug doses sealed within blisters on a blister disk. A plunger pierces the blisters, to release each dose. The disk is advanced by a knob with each successive dose. The Spiros inhaler, described in U.S. patent application Ser. No. 08/681,103 is a dry powder inhaler which also uses a blister disk. Another inhaler described in PCT application No. PCT/US93/09751 contains individual medicine doses stored within a plurality of apertures in a medicine containing cartridge. The cartridge is manually advanced to successive doses by rotating the medicine containing cartridge. U.S. Pat. Nos. 5,327,883, and 5,577,497, describe an inhaler having a spinning impeller.

Known devices for delivering aerosol medication for inhalation by a patient include metered dose inhalers that are manually operated and breath actuated. Some Examples of devices for delivering aerosol medication for inhalation are described in U.S. Pat. Nos. 5,960,792; 5,848,587; 5,738,087; 5,666,948; 5,617,844; 5,505,194; 5,394,866; 5290,539; 5,165,391; 5,027,806; 4,955,371; 4,852,561; 4,790,305; 4,509,515; 5,954,047; 5,755,218; 5,724,986; 5,622,162; 5,544,647; 5,505,194; 5,392,768; 5,304,125; 4,852,561; 3,187,748; 3,565,070; 3,814,297; 3,826,413; 4,592,348; 4,648,393; 4,803,978; 4,896,832; a product available from 3M Healthcare known as Aerosol Sheathed Actuator and Cap; and a product available from Riker Laboratories known as Autohaler.

Some Examples of fixed aerosol actuator devices of one-piece construction are described in U.S. Pat. Nos. 3,918,451; 3,991,761; 4,011,864; 4,069,819; 4,227,522; 4,265,236; 4,454,877; 4,576,157; 4,648,393; 4,860,740; 5,002,048; 5,012,804; 5,115,803; 5,134,993; 5,134,993; 5,161,524; and 5,178,138.

Devices which are articulated and which can be folded or telescoped for convenient carrying in a pocket or purse are described in U.S. Pat. Nos. 3,739,950; 3,788,316; 3,927,806; 3,994,421; 4,130,116; 4,292,966; 4,509,515; 4,637,528; and 4,641,644.

Breath activated inhalers differ from pressurized aerosol inhalers in that breath activated inhalers are activated by inhalation of the user so that the drug is reliably drawn into the distal regions of the lung. Typical breath activated inhalers are described in U.S. Pat. Nos. 6,102,036; 5,483,954; 4,846,168; 4,524,769. Other systems also include a means of triggering the medication release by the start of inhalation. Such devices have been described in U.S. Pat. Nos. 4,664,107; 4,803,978 and 4,739,754.

Some disposable, breath-actuated inhalers are described in WO 89/01348, U.S. Pat. No. 4,265,236. Other disposable inhalers are described in U.S. Pat. Nos. 6,102,035, 6,062,213, 5,660,169, 5,533,505, 4,955,371.

Other more recent improvements in inhalers are described in U.S. Pat. Nos. 6,149,892; 6,143,277; 6,131,566; 6,116,234; 6,062,213; 6,083,514; 6,074,668; and 5,878,917.

All of the disclosures of these aforementioned patents are hereby incorporated by reference in their entireties.

The invention claimed is:

1. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises a drum having an inner cavity disposed therein for containing said multiparticulates, said drum having an outer lining, a rotatable inner lining disposed immediately within the outer lining and a stationary retaining strip located immediately within a portion of said inner lining;

said outer lining having a dispensing hole at a point behind the retaining strip to dispense said unit dose;

said rotating inner lining having a filling hole disposed therein and having a first position where said filling hole is not adjacent to said retaining strip to allow a unit dose of said multiparticulates to be filled therein;

said rotating inner lining having a second position where said filling hole is adjacent to said retaining strip and in communication with said outer hole, wherein said unit dose is delivered from the reservoir to said dispensing hole when the inner lining is moved from said first position to said second position upon actuation and the unit dose is expelled from the device.

2. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises a reservoir to contain said multiparticulates, said reservoir having an exit hole therein;

a rotatable member outside said reservoir having an external cavity in communication with said exit hole when said rotatable member is in a first position to allow a unit dose of said multiparticulates to be filled therein;

a stationary retaining housing immediately covering said rotating member, said retaining housing having a dispensing hole disposed therein;

said rotatable member having a second position wherein said external cavity of said rotatable member is in communication with said dispensing hole wherein said unit dose is delivered from the reservoir to said dispensing hole when the rotatable member is moved from said first position to said second position upon actuation and the unit dose is expelled from the device.

3. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises a reservoir to contain said multiparticulates, said reservoir having an exit hole therein;

a rotatable member outside said reservoir having a plurality of external cavities;

a stationary retaining housing immediately covering said rotating member, said retaining housing having a dispensing hole disposed therein;

said rotatable member in position wherein one external cavity is in communication with said exit hole to be filled with a unit dose of said multiparticulates and one external cavity is in communication with said dispensing hole;

said rotating member rotatable to advance each cavity to the exact position of the next adjacent cavity upon actuation, wherein a unit dose of said multiparticulates is delivered from said dispensing hole when a cavity containing said unit dose is advanced to be in communication with said dispensing hole.

4. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises a reservoir to contain said multiparticulates, said reservoir having an exit hole therein;

a movable plate having a filling hole disposed therein, said movable plate having a first position wherein said filling hole is in communication with said exit hole of said reservoir;

a stationary retaining plate immediately under said movable plate to form a filling cavity with said filling hole to be filled with a unit dose of multiparticulates when said movable plate is in said first position, said stationary retaining plate having a dispensing hole;

said movable plate having a second position wherein said filling hole is in communication with said dispensing hole and said unit dose is dispensed from said device, wherein said moving plate moves from said first position to said second position upon actuation.

5. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises a reservoir to contain said multiparticulates, said reservoir having an exit hole therein;

a movable plate having a filling hole disposed therein, said movable plate having a first position wherein said filling hole is in communication with said exit hole of said reservoir;

a stationary retaining plate immediately under said movable plate to form a filling cavity with said filling hole to be filled with a unit dose of multiparticulates when said movable plate is in said first position, said stationary retaining plate having a dispensing hole;

said movable plate having a second position wherein said filling hole is in communication with said dispensing hole and said unit dose is dispensed from said device, wherein said moving plate moves from said first position to said second position upon actuation, wherein said device has a stationary upper plate immediately over said movable plate having a hole therein in communication with said reservoir hole and said filling hole.

6. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device comprises
  a reservoir to contain said multiparticulates, said reservoir having an exit hole therein;
  a movable plate having a filling hole disposed therein, said movable plate having a first position wherein said filling hole is in communication with said exit hole of said reservoir;
  a stationary retaining plate immediately under said movable plate to form a filling cavity with said filling hole to be filled with a unit dose of multiparticulates when said movable plate is in said first position, said stationary retaining plate having a dispensing hole;
  said movable plate having a second position wherein said filling hole is in communication with said dispensing hole and said unit dose is dispensed from said device, wherein said moving plate moves from said first position to said second position upon actuation, wherein said movable plate is rectangular and slidably moves from said first position to said second position.

7. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 µm to about 1 mm such that an effective dose of said drug cannot be delivered into the lower lung of a human patient, wherein said device comprises
  a reservoir to contain said multiparticulates, said reservoir having an exit hole therein;
  a movable plate having a filling hole disposed therein, said movable plate having a first position wherein said filling hole is in communication with said exit hole of said reservoir;
  a stationary retaining plate immediately under said movable plate to form a filling cavity with said filling hole to be filled with a unit dose of multiparticulates when said movable plate is in said first position, said stationary retaining plate having a dispensing hole;
  said movable plate having a second position wherein said filling hole is in communication with said dispensing hole and said unit dose is dispensed from said device, wherein said moving plate moves from said first position to said second position upon actuation, wherein said movable plate is circular and rotatably moves from said first position to said second position.

8. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein
  said housing has an inner cavity formed therein for containing multiple doses of said multiparticulates, said housing having a tapered top end with an opening therein and a tapered bottom end; and further comprising
  a lifting rod fitted at a first position within the tapered bottom end of the housing which is movable to a second position within the tapered top end of the housing, said lifting rod comprising an elongated cylinder with a top end and an inner push rod within the elongated cylinder which terminates at a point below the top end of the cylinder to form a filling cavity when the lifting rod is in the first position, said inner push rod movable to terminate at a point above the top end of the cylinder when the lifting rod is at the second position;
  wherein when the device is upright in the first position, said filling cavity is filled with a unit dose of said multiparticulates and when the lifting rod is moved to the second position upon actuation, the inner push rod moves to a point above the top end of the cylinder and the unit dose is delivered from the housing.

9. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein
  said housing has an inner cavity formed therein for containing multiple doses of said multiparticulates, said housing having a tapered top end with an opening therein and a tapered bottom end; and further comprising
  a lifting rod fitted at a first position within the tapered bottom end of the housing which is movable to a second position within the tapered top end of the housing, said lifting rod comprising an elongated cylinder with a top end and an inner push rod within the elongated cylinder which terminates at a point below the top end of the cylinder to form a filling cavity when the lifting rod is in the first position, said inner push rod movable to terminate at a point above the top end of the cylinder when the lifting rod is at the second position;
  wherein when the device is upright in the first position, said filling cavity is filled with a unit dose of said multiparticulates and when the lifting rod is moved to the second position upon actuation, the inner push rod moves to a point above the top end of the cylinder and the unit dose is delivered from the housing, and further comprising an inner ridge in the opening of the tapered top end, said inner ridge configured to engage and stop the motion of the elongated cylinder and not the inner push rod, allowing said inner push rod to terminate at a point above the top end of the cylinder to expel the unit dose.

10. A device for delivery of a drug, for gastrointestinal deposition, comprising a housing and an actuator, said device capable of containing multiple doses of multiparticulates comprising drug particles, said device upon
  actuation capable of delivering a unit dose of said multiparticulates wherein said drug particles have a mean diameter of greater than 10 µm to about 1 mm such that an effective dose of said drug cannot be delivered into the lower lung of a human patient, wherein
  said housing has an inner cavity formed therein for containing multiple doses of said multiparticulates, said housing having a tapered top end with an opening therein and a tapered bottom end; and further comprising
  a lifting rod fitted at a first position within the tapered bottom end of the housing which is movable to a second position within the tapered top end of the housing, said lifting rod comprising an elongated cylinder with a top end and an inner push rod within the elongated cylinder which terminates at a point below the top end of the cylinder to form a filling cavity when the lifting rod is in the first position, said inner push rod movable to terminate at a point above the top end of the cylinder when the lifting rod is at the second position; wherein when the device is upright in the first position, said filling cavity is filled with a unit dose of said multiparticulates and when the lifting rod is moved to the second position upon actuation, the inner push rod moves to a point above the top end of the cylinder and the unit dose is delivered from the housing, and wherein the placement of the inner push rod in the elongated cylinder at the first position is adjustable in order to vary the volume of the filling cavity and individualize the dose of said drug.

11. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein said housing has an inner cavity, said housing having an opening connecting the inner cavity to outside of said housing, said housing adapted to fit within the oral cavity of a human patient with the opening facing the tongue of said patient; and further comprising a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug.

12. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein said housing has an inner cavity, said housing having an opening connecting the inner cavity to outside of said housing, said housing adapted to fit within the oral cavity of a human patient with the opening facing the tongue of said patient; and further comprising a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug, wherein said movable member is horizontally slidable from said first position to said second position.

13. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein said housing has an inner cavity, said housing having an opening connecting the inner cavity to outside of said housing, said housing adapted to fit within the oral cavity of a human patient with the opening facing the tongue of said patient; and further comprising a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug, wherein said movable member is rotatable within said elongated housing and rotates from said first position to said second position.

14. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein said housing has an inner cavity, said housing having an opening connecting the inner cavity to outside of said housing, said housing adapted to fit within the oral cavity of a human patient with the opening facing the tongue of said patient; and further comprising a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug, and further comprising a powder feeder coupled to said opening of said housing to deposit a unit dose of drug into said aperture when said movable member is in the second position, said powder feeder removable from said opening of said housing in order to allow for the deposit of said dose onto the tongue of said patient.

15. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein said housing has an inner cavity, said housing having an opening connecting the inner cavity to outside of said housing, said housing adapted to fit within the oral cavity of a human patient with the opening facing the tongue of said patient; and further comprising a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug, and further comprising a powder feeder coupled to said opening of said housing to deposit a unit dose of drug into said aperture when said movable member is in the second position, said powder feeder removable from said opening of said housing in order to allow for the deposit of said dose onto the tongue of said patient, wherein said powder feeder is removable from the housing.

16. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient, wherein
said housing has an inner cavity, said housing having an opening connecting the inner cavity to outside of said housing, said housing adapted to fit within the oral cavity of a human patient with the opening facing the tongue of said patient; and further comprising
a movable member within said inner cavity, said movable member having a filling aperture capable of containing a dose of drug, said filling aperture enclosed by said housing when said movable member is in a first position, said movable member capable of being positioned to a second position wherein said filling aperture is in communication with said housing opening to load said drug into said aperture or to deliver said drug, and further comprising a powder feeder coupled to said opening of said housing to deposit a unit dose of drug into said aperture when said movable member is in the second position, said powder feeder removable from said opening of said housing in order to allow for the deposit of said dose onto the tongue of said patient, wherein said powder feeder is attached to said housing by a folding member.

17. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient,
wherein said housing has a reservoir and a shaft in communication with said reservoir, said housing having an opening connecting the shaft to outside of said housing, said housing adapted to fit within the oral cavity of a human patient with the opening facing the tongue of said patient;
a movable member having a filling aperture capable of containing a dose of drug, said movable member fitted within said shaft in a first position wherein said filling aperture is in communication with said reservoir and capable of being filled with said dose, said movable member capable of being positioned to a second position upon actuation with said filling aperture in communication with said housing opening wherein the dose of drug is delivered.

18. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient,
wherein said housing has a reservoir and a shaft in communication with said reservoir, said housing having an opening connecting the shaft to outside of said housing, said housing adapted to fit within the oral cavity of a human patient with the opening facing the tongue of said patient;
a movable member having a filling aperture capable of containing a dose of drug, said movable member fitted within said shaft in a first position wherein said filling aperture is in communication with said reservoir and capable of being filled with said dose, said movable member capable of being positioned to a second position upon actuation with said filling aperture in communication with said housing opening wherein the dose of drug is delivered,
wherein said movable member is horizontally slidable from said first position to said second position.

19. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 µm to about 1 mm such that an effective dose of said drug cannot be delivered into the lower lung of a human patient,
wherein said housing has a reservoir and a shaft in communication with said reservoir, said housing having an opening connecting the shaft to outside of said housing, said housing adapted to fit within the oral cavity of a human patient with the opening facing the tongue of said patient;
a movable member having a filling aperture capable of containing a dose of drug, said movable member fitted within said shaft in a first position wherein said filling aperture is in communication with said reservoir and capable of being filled with said dose, said movable member capable of being positioned to a second position upon actuation with said filling aperture in communication with said housing opening wherein the dose of drug is delivered,
wherein said movable member is rotatable within said elongated housing and rotates from said first position to said second position.

20. A method for delivery of a drug for gastrointestinal deposition, comprising delivering multiparticulates comprising drug particles via the use of a multiple unit dosing device comprising a housing and an actuator, said device upon actuation delivering a unit dose of said multiparticulates, and thereafter re-using said device to deliver additional unit doses of said drug at appropriate dosing intervals, said drug particles having a mean particle size of greater than 10 µm to about 1 mm such that an effective dose of said drug cannot be delivered into the lower lung of a human patient, wherein said delivery is by dispensing ex vivo said unit dose into an intermediate receptacle.

21. A method of administering a drug to a human patient for gastrointestinal deposition comprising formulating said drug in a non-compressed multiparticulate form;

containing said multiparticulates in a drug delivery device capable of administering multiple unit doses of said multiparticulates into the oral cavity;

administering a unit dose of the multiparticulates to the oral cavity wherein greater than about 80% of the unit dose is deposited in the gastrointestinal tract.

22. The method of claim 21 wherein greater than about 90% of the drug is deposited in the gastrointestinal tract.

23. The method of claim 21 wherein about 100% of the drug is deposited in the gastrointestinal tract.

24. A method of preparing a drug delivery system for delivering multiple doses of a drug for gastrointestinal deposition comprising preparing non-compressed multiparticulates comprising drug particles in a manner wherein said drug particles, when placed in the oral cavity and swallowed are deposited to the gastrointestinal tract and not deposited in any substantial amount to the lungs; and placing multiple unit doses of said multiparticulates in a device which meters a single unit dose for delivery.

25. A method of treating a patient in need of multiple doses of a drug for gastrointestinal deposition comprising preparing non-compressed multiparticulates comprising drug particles, wherein said drug particles, when placed in the oral cavity and swallowed are deposited to the gastrointestinal tract and not deposited in any substantial amount to the lungs;

placing multiple unit doses of said multiparticulates in a device which meters a single unit dose for delivery; and either (a) administering said unit dose into the oral cavity of a patient or (b) dispensing said unit dose into an intermediate receptacle and thereafter administering said unit dose into the oral cavity of said patient.

26. A drug delivery system for gastrointestinal deposition, comprising a multiple unit dosing device comprising a housing and an actuator, said device containing multiple doses of multiparticulates comprising drug particles, said device upon actuation delivering a unit dose of said multiparticulates, said drug particles having a mean diameter of greater than 10 μm to about 1 mm such that an effective dose of said drug cannot be delivered into the lower lung of a human patient, wherein said device delivers greater than 80%, preferably greater than about 90% and preferably about 100% of the unit dose in a downward direction within about 45 degrees to about 135 degrees from horizontal, based on a vertical baseline independent of the device.

27. A device for delivery of a drug, for gastrointestinal deposition, comprising a housing and an actuator, said device capable of containing multiple doses of multiparticulates comprising drug particles, said device upon actuation capable of delivering a unit dose of said multiparticulates wherein said drug particles have a mean diameter of greater than 10 μm to about 1 mm such that an effective dose of said drug cannot be delivered into the lower lung of a human patient, wherein said device can deliver greater than 80%, preferably greater than about 90% and preferably about 100% of the unit dose in a downward direction within about 45 degrees to about 135 degrees from horizontal, based on a vertical baseline independent of the device.

* * * * *